United States Patent
Hassler, Jr. et al.

(10) Patent No.: US 8,016,745 B2
(45) Date of Patent: *Sep. 13, 2011

(54) MONITORING OF A FOOD INTAKE RESTRICTION DEVICE

(75) Inventors: William L. Hassler, Jr., Cincinnati, OH (US); Daniel F. Dlugos, Morrow, OH (US); Dustin R. Jensen, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 543 days.

This patent is subject to a terminal disclaimer.

(21) Appl. No.: 11/398,940

(22) Filed: Apr. 6, 2006

(65) Prior Publication Data

US 2006/0199997 A1    Sep. 7, 2006

Related U.S. Application Data

(63) Continuation-in-part of application No. 11/167,861, filed on Jun. 24, 2005, and a continuation-in-part of application No. 11/065,410, filed on Feb. 24, 2005, now Pat. No. 7,699,770.

(51) Int. Cl.
*A61F 2/00* (2006.01)
(52) U.S. Cl. ...................................................... 600/37
(58) Field of Classification Search .......... 128/897–899; 600/29–32, 37, 593; 604/27–28, 909; 606/139–141, 606/157, 201–203, 213, 228, 151; 607/41
See application file for complete search history.

(56) References Cited

U.S. PATENT DOCUMENTS

| | | |
|---|---|---|
| RE03,036 E | 7/1868 | Shunk |
| RE03,037 E | 7/1868 | Tucker |
| RE03,115 E | 9/1868 | Lewis |
| RE03,187 E | 11/1868 | Winchester |
| RE03,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |

(Continued)

FOREIGN PATENT DOCUMENTS

AU    729 467    2/2001

(Continued)

OTHER PUBLICATIONS

Lechner, Wolfgang, et al.—"In Vivo Band Manometry: a New Access to Band Adjustment"—*Obesity Surgery*, 15,1432-1436—2005.

(Continued)

*Primary Examiner* — John Lacyk
(74) *Attorney, Agent, or Firm* — Dean L. Garner

(57) ABSTRACT

An implantable restriction device is configured to provide a restriction in a patient as a function of the pressure of fluid. The implantable restriction device includes one or more pressure sensors configured to sense pressure of the fluid within the implantable restriction device. Pressure data obtained by the one or more pressure sensors may be communicated to a device located external to the patient, such as a data logger, using telemetry coils or other communicators. The data logger may store the pressure data, and may communicate the pressure data to a remote location via a network such as the Internet. A docking station may be provided to couple the data logger to a network and/or to recharge a cell in the data logger.

15 Claims, 14 Drawing Sheets

U.S. PATENT DOCUMENTS

| | | |
|---|---|---|
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff et al. |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,178,463 A | 10/1939 | Bahnson |
| 2,180,599 A | 11/1939 | Menasco |
| 2,177,564 A | 12/1939 | Havill |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,396,351 A | 3/1946 | Thompson |
| 2,426,392 A | 8/1947 | Fennema |
| 2,426,817 A | 9/1947 | Carlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Harley |
| 3,057,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |

| | | | | | | |
|---|---|---|---|---|---|---|
| 3,182,494 A | 5/1965 | Beatty et al. | | 3,478,344 A | 11/1969 | Schwitzgebel et al. |
| 3,187,181 A | 6/1965 | Keller | | 3,482,449 A | 12/1969 | Werner |
| 3,187,745 A | 6/1965 | Baum et al. | | 3,482,816 A | 12/1969 | Arnold |
| 3,190,388 A | 6/1965 | Moser et al. | | 3,487,959 A | 1/1970 | Pearne et al. |
| 3,205,547 A | 9/1965 | Riekse | | 3,491,842 A | 1/1970 | Delacour et al. |
| 3,208,255 A | 9/1965 | Burk | | 3,492,638 A | 1/1970 | Lane |
| 3,209,570 A | 10/1965 | Hills | | 3,502,829 A | 3/1970 | Reynolds |
| 3,221,468 A | 12/1965 | Casey | | 3,503,116 A | 3/1970 | Strack |
| 3,228,703 A | 1/1966 | Wilson | | 3,504,664 A | 4/1970 | Haddad |
| 3,229,684 A | 1/1966 | Nagumo et al. | | 3,505,808 A | 4/1970 | Eschle |
| 3,236,088 A | 2/1966 | Moller | | 3,509,754 A | 5/1970 | Massingill et al. |
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,489 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,424 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,615 A | 4/1973 | Lenzkes |
| 3,472,230 A | 10/1969 | Fogarty | | 3,730,174 A | 5/1973 | Madison |

| | | | | | |
|---|---|---|---|---|---|
| 3,730,560 A | 5/1973 | Abildgaard et al. | 3,904,234 A | 9/1975 | Hill et al. |
| 3,731,679 A | 5/1973 | Wilhelmson et al. | 3,908,334 A | 9/1975 | Rychiger et al. |
| 3,731,681 A | 5/1973 | Blackshear et al. | 3,908,461 A | 9/1975 | Turpen |
| 3,732,731 A | 5/1973 | Fussell, Jr. | 3,908,721 A | 9/1975 | McGahey et al. |
| 3,735,040 A | 5/1973 | Punt et al. | 3,910,087 A | 10/1975 | Jones |
| 3,736,930 A | 6/1973 | Georgi | 3,912,168 A | 10/1975 | Mullins et al. |
| 3,738,356 A | 6/1973 | Workman | 3,912,304 A | 10/1975 | Abildgaard et al. |
| 3,740,921 A | 6/1973 | Meyer et al. | 3,918,286 A | 11/1975 | Whitehead |
| 3,746,111 A | 7/1973 | Berthiaume et al. | 3,918,291 A | 11/1975 | Pauly et al. |
| 3,748,678 A | 7/1973 | Ballou | 3,920,965 A | 11/1975 | Sohrwardy et al. |
| 3,749,098 A | 7/1973 | De Bennetot et al. | 3,921,682 A | 11/1975 | McGahey et al. |
| 3,749,422 A | 7/1973 | Abildgaard et al. | 3,922,951 A | 12/1975 | Linsinger et al. |
| 3,749,423 A | 7/1973 | Abildgaard et al. | 3,923,060 A | 12/1975 | Ellinwood, Jr. |
| 3,750,194 A | 8/1973 | Summers | 3,924,635 A | 12/1975 | Hakim et al. |
| 3,757,770 A | 9/1973 | Brayshaw et al. | 3,928,980 A | 12/1975 | Ganzinotti et al. |
| 3,759,095 A | 9/1973 | Short, Jr. et al. | 3,929,175 A | 12/1975 | Coone |
| 3,760,638 A | 9/1973 | Lawson et al. | 3,930,682 A | 1/1976 | Booth |
| 3,763,960 A | 10/1973 | John et al. | 3,930,852 A | 1/1976 | Tanaka et al. |
| 3,765,142 A | 10/1973 | Lindquist et al. | 3,936,028 A | 2/1976 | Norton et al. |
| 3,765,494 A | 10/1973 | Kielman, Jr. | 3,939,823 A | 2/1976 | Kaye et al. |
| 3,769,156 A | 10/1973 | Brecy et al. | 3,940,122 A | 2/1976 | Janzen et al. |
| 3,769,830 A | 11/1973 | Porter et al. | 3,940,630 A | 2/1976 | Bergonz |
| 3,774,243 A | 11/1973 | Ny et al. | 3,942,299 A | 3/1976 | Bory et al. |
| 3,776,333 A | 12/1973 | Mathauser | 3,942,382 A | 3/1976 | Hok et al. |
| 3,778,051 A | 12/1973 | Allen et al. | 3,942,536 A | 3/1976 | Mirowski et al. |
| 3,780,578 A | 12/1973 | Sellman et al. | 3,943,915 A | 3/1976 | Severson |
| 3,781,902 A | 12/1973 | Shim et al. | 3,945,704 A | 3/1976 | Kraus et al. |
| 3,783,585 A | 1/1974 | Hoyland et al. | 3,946,613 A | 3/1976 | Silver |
| 3,789,667 A | 2/1974 | Porter et al. | 3,946,615 A | 3/1976 | Hluchan |
| 3,796,095 A | 3/1974 | Fussell, Jr. | 3,946,724 A | 3/1976 | La Balme et al. |
| 3,807,219 A | 4/1974 | Wallskog | 3,948,141 A | 4/1976 | Shinjo et al. |
| 3,811,429 A | 5/1974 | Fletcher et al. | 3,949,388 A | 4/1976 | Fuller |
| 3,815,722 A | 6/1974 | Sessoms | 3,953,289 A | 4/1976 | Costes et al. |
| 3,818,765 A | 6/1974 | Eriksen et al. | 3,954,271 A | 5/1976 | Tredway, Sr. |
| 3,820,400 A | 6/1974 | Russo | 3,958,558 A | 5/1976 | Dunphy et al. |
| 3,820,795 A | 6/1974 | Taylor | 3,960,142 A | 6/1976 | Elliott et al. |
| 3,823,610 A | 7/1974 | Fussell, Jr. | 3,961,425 A | 6/1976 | Swanson et al. |
| 3,825,065 A | 7/1974 | Lloyd et al. | 3,961,646 A | 6/1976 | Schon et al. |
| 3,825,963 A | 7/1974 | Abildgaard et al. | 3,962,895 A | 6/1976 | Rydell |
| 3,825,964 A | 7/1974 | Groswith, III et al. | 3,962,921 A | 6/1976 | Lips |
| 3,828,672 A | 8/1974 | Gazzola et al. | 3,963,019 A | 6/1976 | Quandt |
| 3,828,766 A | 8/1974 | Krasnow | 3,964,485 A | 6/1976 | Neumeier |
| 3,831,588 A | 8/1974 | Rindner | 3,964,770 A | 6/1976 | Abildgaard et al. |
| 3,831,942 A | 8/1974 | Del Mar | 3,967,737 A | 7/1976 | Peralta et al. |
| 3,833,238 A | 9/1974 | Liard et al. | 3,968,473 A | 7/1976 | Patton et al. |
| 3,834,167 A | 9/1974 | Tabor | 3,968,594 A | 7/1976 | Kawakami |
| 3,834,739 A | 9/1974 | Abildgaard et al. | 3,972,320 A | 8/1976 | Kalman |
| 3,835,523 A | 9/1974 | Stansfield et al. | 3,973,753 A | 8/1976 | Wheeler |
| 3,839,708 A | 10/1974 | Bredesen et al. | 3,973,858 A | 8/1976 | Poisson et al. |
| 3,842,483 A | 10/1974 | Cramer | 3,974,655 A | 8/1976 | Halpern et al. |
| 3,842,668 A | 10/1974 | Lippke et al. | 3,974,865 A | 8/1976 | Fenton et al. |
| 3,845,664 A | 11/1974 | Perry, Jr. | 3,976,278 A | 8/1976 | Dye et al. |
| 3,845,751 A | 11/1974 | Runstetler | 3,977,391 A | 8/1976 | Fleischmann |
| 3,845,757 A | 11/1974 | Weyer | 3,980,871 A | 9/1976 | Lindstrom et al. |
| 3,847,434 A | 11/1974 | Weman et al. | 3,982,571 A | 9/1976 | Fenton et al. |
| 3,850,208 A | 11/1974 | Hamilton | 3,983,948 A | 10/1976 | Jeter |
| 3,853,117 A | 12/1974 | Murr | 3,985,133 A | 10/1976 | Jenkins et al. |
| 3,854,469 A | 12/1974 | Giori et al. | 3,987,860 A | 10/1976 | Jabsen |
| 3,855,902 A | 12/1974 | Kirst et al. | 3,989,005 A | 11/1976 | Bowler, Jr. et al. |
| 3,857,399 A | 12/1974 | Zacouto et al. | 3,991,749 A | 11/1976 | Zent |
| 3,857,452 A | 12/1974 | Hartman | 3,992,948 A | 11/1976 | D'Antonio et al. |
| 3,857,745 A | 12/1974 | Grausch et al. | 3,993,149 A | 11/1976 | Harvey |
| 3,858,581 A | 1/1975 | Kamen | 3,996,927 A | 12/1976 | Frank |
| 3,863,622 A | 2/1975 | Buuck | 3,996,962 A | 12/1976 | Sutherland |
| 3,863,933 A | 2/1975 | Tredway | 4,003,141 A | 1/1977 | Le Roy |
| 3,867,950 A | 2/1975 | Fischell | 4,005,282 A | 1/1977 | Jennings |
| 3,868,008 A | 2/1975 | Brumbaugh | 4,005,593 A | 2/1977 | Goldberg |
| 3,868,679 A | 2/1975 | Arneson | 4,006,735 A | 2/1977 | Hittman et al. |
| 3,871,599 A | 3/1975 | Takada et al. | 4,009,591 A | 3/1977 | Hester |
| 3,872,285 A | 3/1975 | Shum et al. | 4,010,449 A | 3/1977 | Faggin et al. |
| 3,874,388 A | 4/1975 | King et al. | 4,014,319 A | 3/1977 | Favre et al. |
| 3,876,980 A | 4/1975 | Haemmig et al. | 4,014,321 A | 3/1977 | March |
| 3,878,908 A | 4/1975 | Andersson et al. | 4,016,764 A | 4/1977 | Rice |
| 3,881,528 A | 5/1975 | Mackenzie | 4,017,329 A | 4/1977 | Larson |
| 3,886,948 A | 6/1975 | Hakim et al. | 4,018,134 A | 4/1977 | Linsinger et al. |
| 3,893,111 A | 7/1975 | Cotter | 4,022,190 A | 5/1977 | Meyer |
| 3,893,451 A | 7/1975 | Durand et al. | 4,024,864 A | 5/1977 | Davies et al. |
| 3,895,681 A | 7/1975 | Griffin et al. | 4,025,912 A | 5/1977 | Rice |
| 3,899,862 A | 8/1975 | Muys et al. | 4,026,276 A | 5/1977 | Chubbuck |

| Patent No. | Date | Name |
|---|---|---|
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,296 A | 9/1977 | Ishida et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal et al. |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer et al. |
| 4,114,424 A | 9/1978 | Johnson |
| 4,114,603 A | 9/1978 | Wilkinson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,135,509 A | 1/1979 | Shannon |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,173,228 A | 11/1979 | Van Steenwyk et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel et al. |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori et al. |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori et al. |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |
| 4,332,254 A | 6/1982 | Lundquist |
| 4,332,255 A | 6/1982 | Hakim et al. |
| 4,339,831 A | 7/1982 | Johnson |
| 4,342,218 A | 8/1982 | Fox |

| | | |
|---|---|---|
| 4,342,308 A | 8/1982 | Trick |
| 4,346,604 A | 8/1982 | Snook et al. |
| 4,347,851 A | 9/1982 | Jundaniam |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Schimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,715 A | 6/1983 | Hakim et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons et al. |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,124 A | 12/1983 | Marshall |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,450,946 A | 5/1984 | Olding et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush et al. |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,551,128 A | 11/1985 | Hakim et al. |
| 4,552,150 A | 11/1985 | Zacouto et al. |
| 4,553,226 A | 11/1985 | Scherbatskoy |
| 4,556,063 A | 12/1985 | Thompson et al. |
| 4,556,086 A | 12/1985 | Raines |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,749 A | 2/1986 | Fischell |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,595,390 A | 6/1986 | Hakim et al. |
| 4,596,563 A | 6/1986 | Pande |
| 4,599,943 A | 7/1986 | Kobler et al. |

| Patent | Date | Name |
|---|---|---|
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,615,691 A | 10/1986 | Hakim et al. |
| 4,617,016 A | 10/1986 | Blomberg et al. |
| 4,618,861 A | 10/1986 | Gettens et al. |
| 4,620,807 A | 11/1986 | Polit |
| 4,621,331 A | 11/1986 | Iwata et al. |
| 4,622,871 A | 11/1986 | Van Sickle et al. |
| 4,626,462 A | 12/1986 | Kober et al. |
| 4,633,304 A | 12/1986 | Nagasaki et al. |
| 4,633,878 A | 1/1987 | Bombardieri et al. |
| 4,635,182 A | 1/1987 | Hintz |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zehuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,711,249 A | 12/1987 | Brooks |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,727,887 A | 3/1988 | Haber |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,257 A | 9/1988 | Hakim et al. |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,785,822 A | 11/1988 | Wallace |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,799,491 A | 1/1989 | Eckerle |
| 4,799,625 A | 1/1989 | Weaver, Jr. et al. |
| 7,987,227 B1 | 1/1989 | Goodwin |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasue et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio |
| 4,893,630 A | 1/1990 | Bray, Jr. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,905,698 A | 3/1990 | Strohl, Jr. et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |

| Patent No. | Date | Inventor(s) |
|---|---|---|
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,884 A | 4/1991 | Ohta et al. |
| 5,006,997 A | 4/1991 | Reich |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,099,845 A | 3/1992 | Besz et al. |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,120,313 A | 6/1992 | Elftman |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bangmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,163,904 A | 11/1992 | Lampropoulos et al. |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirige et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |

| | | |
|---|---|---|
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Wallock |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,396,899 A | 3/1995 | Strittmatter |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,425,713 A | 6/1995 | Taylor et al. |
| 5,431,171 A | 7/1995 | Harrison et al. |
| 5,431,629 A | 7/1995 | Lampropoulos et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,345 A | 9/1995 | Taylor et al. |
| 5,449,368 A | 9/1995 | Kuzmak |
| 5,456,690 A | 10/1995 | Duong-Van |
| 5,461,293 A | 10/1995 | Rozman et al. |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,490,514 A | 2/1996 | Rosenberg |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,540,731 A | 7/1996 | Testerman |
| 5,541,857 A | 7/1996 | Walter et al. |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,591,171 A | 1/1997 | Brown |
| 5,592,939 A | 1/1997 | Martinelli |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,622,869 A | 4/1997 | Lewis et al. |
| 5,625,946 A | 5/1997 | Wildeson et al. |
| 5,626,623 A | 5/1997 | Kieval et al. |
| 5,626,630 A | 5/1997 | Markowitz et al. |

| | | | | | |
|---|---|---|---|---|---|
| 5,630,836 A | 5/1997 | Prem et al. | 5,967,986 A | 10/1999 | Cimochowski et al. |
| 5,634,255 A | 6/1997 | Bishop et al. | 5,970,801 A | 10/1999 | Ciobanu et al. |
| 5,637,083 A | 6/1997 | Bertrand et al. | 5,971,934 A | 10/1999 | Scherer et al. |
| 5,643,207 A | 7/1997 | Rise | 5,974,873 A | 11/1999 | Nelson et al. |
| 5,645,065 A | 7/1997 | Shapiro et al. | 5,978,985 A | 11/1999 | Thurman |
| 5,645,116 A | 7/1997 | McDonald | 5,993,395 A | 11/1999 | Shulze |
| 5,650,766 A | 7/1997 | Burgmann et al. | 5,993,398 A | 11/1999 | Alperin |
| 5,673,585 A | 10/1997 | Bishop et al. | 5,995,874 A | 11/1999 | Borza et al. |
| 5,676,690 A | 10/1997 | Noren et al. | 6,009,878 A | 1/2000 | Weijand et al. |
| 5,681,285 A | 10/1997 | Ford et al. | 6,010,482 A | 1/2000 | Kriesel et al. |
| 5,686,831 A | 11/1997 | Vandervalk et al. | 6,015,386 A | 1/2000 | Kensey et al. |
| 5,687,734 A | 11/1997 | Dempsey et al. | 6,015,387 A | 1/2000 | Schwartz et al. |
| 5,693,076 A | 12/1997 | Kaemmerer | 6,019,729 A | 2/2000 | Itoigawa et al. |
| 5,702,368 A | 12/1997 | Stevens et al. | 6,024,704 A | 2/2000 | Meador et al. |
| 5,702,427 A | 12/1997 | Ecker et al. | 6,030,413 A | 2/2000 | Lazarus |
| 5,702,431 A | 12/1997 | Wang et al. | 6,035,461 A | 3/2000 | Nguyen |
| 5,704,352 A | 1/1998 | Tremblay et al. | 6,053,873 A | 4/2000 | Govari et al. |
| 5,711,302 A | 1/1998 | Lampropoulos et al. | 6,056,723 A | 5/2000 | Donlon |
| 5,715,786 A | 2/1998 | Seiberth et al. | 6,058,330 A | 5/2000 | Borza et al. |
| 5,715,837 A | 2/1998 | Chen | 6,059,757 A | 5/2000 | Macoviak et al. |
| 5,716,342 A | 2/1998 | Dumbraveanu et al. | 6,067,474 A | 5/2000 | Schulman et al. |
| 5,720,436 A | 2/1998 | Buschor et al. | 6,067,991 A | 5/2000 | Forsell et al. |
| 5,721,382 A | 2/1998 | Kriesel et al. | 6,071,267 A | 6/2000 | Zamierowski |
| 5,730,101 A | 3/1998 | Aupperle et al. | 6,076,016 A | 6/2000 | Feierbach |
| 5,732,710 A | 3/1998 | Rabinovich et al. | 6,083,174 A | 7/2000 | Brehmeier-Flick et al. |
| 5,733,313 A | 3/1998 | Barreras, Sr. et al. | 6,087,831 A | 7/2000 | Bornert et al. |
| 5,738,652 A | 4/1998 | Boyd et al. | 6,090,096 A | 7/2000 | St. Goar et al. |
| 5,742,233 A | 4/1998 | Hoffman et al. | 6,102,678 A | 8/2000 | Peciat et al. |
| 5,743,267 A | 4/1998 | Nikolic et al. | 6,102,856 A | 8/2000 | Groff et al. |
| 5,749,369 A | 5/1998 | Rabinovich et al. | 6,102,922 A | 8/2000 | Jakobsson et al. |
| 5,749,909 A | 5/1998 | Schroeppel et al. | 6,106,477 A | 8/2000 | Meisel et al. |
| 5,755,687 A | 5/1998 | Donion | 6,106,551 A | 8/2000 | Crossett et al. |
| 5,755,748 A | 5/1998 | Borza et al. | 6,110,145 A | 8/2000 | Macoviak |
| 5,765,568 A | 6/1998 | Sweezer, Jr. et al. | 6,113,553 A | 9/2000 | Chubbuck |
| 5,769,812 A | 6/1998 | Stevens et al. | 6,131,664 A | 10/2000 | Sonnier |
| 5,771,903 A | 6/1998 | Jakobsson | 6,135,945 A | 10/2000 | Sultan |
| 5,782,774 A | 7/1998 | Shmulewitz | 6,152,885 A | 11/2000 | Taepke |
| 5,787,520 A | 8/1998 | Dunbar | 6,158,965 A | 12/2000 | Butterfield et al. |
| 5,791,344 A | 8/1998 | Schulman et al. | 6,159,156 A | 12/2000 | Van Bockel et al. |
| 5,792,094 A | 8/1998 | Stevens et al. | 6,162,180 A | 12/2000 | Miesel et al. |
| 5,792,179 A | 8/1998 | Sideris | 6,162,245 A | 12/2000 | Jayaraman et al. |
| 5,795,325 A | 8/1998 | Valley et al. | 6,168,614 B1 | 1/2001 | Andersen et al. |
| 5,796,827 A | 8/1998 | Coppersmith et al. | 6,171,252 B1 | 1/2001 | Roberts |
| 5,797,403 A | 8/1998 | DiLorenzo | 6,210,347 B1 | 4/2001 | Forsell |
| 5,800,375 A | 9/1998 | Sweezer et al. | 6,216,028 B1 | 4/2001 | Haynor et al. |
| 5,803,917 A | 9/1998 | Butter field et al. | 6,234,745 B1 | 5/2001 | Pugh et al. |
| 5,807,265 A | 9/1998 | Itoigawa et al. | 6,240,316 B1 | 5/2001 | Richmond et al. |
| 5,807,336 A | 9/1998 | Russo et al. | 6,240,318 B1 | 5/2001 | Phillips |
| 5,810,015 A | 9/1998 | Flaherty | 6,245,102 B1 | 6/2001 | Jayaraman |
| 5,810,757 A | 9/1998 | Sweezer, Jr. et al. | 6,248,080 B1 | 6/2001 | Miesel et al. |
| 5,810,841 A | 9/1998 | McNeirney et al. | 6,251,093 B1 | 6/2001 | Valley et al. |
| 5,814,016 A | 9/1998 | Valley et al. | 6,269,819 B1 | 8/2001 | Oz et al. |
| 5,817,093 A | 10/1998 | Williamson, IV et al. | 6,277,078 B1 | 8/2001 | Porat et al. |
| 5,833,603 A | 11/1998 | Kovacs et al. | 6,285,897 B1 | 9/2001 | Kilcoyne et al. |
| 5,836,300 A | 11/1998 | Mault | 6,292,697 B1 | 9/2001 | Roberts |
| 5,836,886 A | 11/1998 | Itoigawa et al. | 6,305,381 B1 | 10/2001 | Weijand et al. |
| 5,840,081 A | 11/1998 | Andersen et al. | 6,309,350 B1 | 10/2001 | VanTassel et al. |
| 5,849,225 A | 12/1998 | Ebina et al. | 6,315,769 B1 | 11/2001 | Peer et al. |
| 5,855,597 A | 1/1999 | Jayaraman et al. | 6,319,208 B1 | 11/2001 | Abita et al. |
| 5,855,601 A | 1/1999 | Bessler et al. | 6,328,699 B1 | 12/2001 | Eigler et al. |
| 5,860,938 A | 1/1999 | Lafontaine et al. | 6,338,735 B1 | 1/2002 | Stevens |
| 5,861,018 A | 1/1999 | Feierbach | 6,357,438 B1 | 3/2002 | Hansen |
| 5,863,366 A | 1/1999 | Snow | 6,360,122 B1 | 3/2002 | Fischell et al. |
| 5,868,702 A | 2/1999 | Stevens et al. | 6,360,822 B1 | 3/2002 | Robertson et al. |
| 5,873,837 A | 2/1999 | Lieber et al. | 6,366,799 B1 | 4/2002 | Acker et al. |
| 5,875,953 A | 3/1999 | Shioya et al. | 6,366,817 B1 | 4/2002 | Kung |
| 5,879,499 A | 3/1999 | Corvi | 6,379,308 B1 | 4/2002 | Brockway et al. |
| 5,881,919 A | 3/1999 | Womac et al. | 6,379,380 B1 | 4/2002 | Satz |
| 5,885,238 A | 3/1999 | Stevens et al. | 6,398,752 B1 | 6/2002 | Sweezer, Jr. et al. |
| 5,887,475 A | 3/1999 | Muldner | 6,409,674 B1 | 6/2002 | Brockway et al. |
| 5,899,927 A | 5/1999 | Ecker et al. | 6,416,291 B1 | 7/2002 | Butterfield et al. |
| 5,916,179 A | 6/1999 | Sharrock | 6,423,031 B1 | 7/2002 | Donlon |
| 5,916,237 A | 6/1999 | Schu | 6,430,444 B1 | 8/2002 | Borza et al. |
| 5,928,182 A | 7/1999 | Kraus et al. | 6,431,175 B1 | 8/2002 | Penner et al. |
| 5,935,078 A | 8/1999 | Feierbach | 6,432,040 B1 | 8/2002 | Meah |
| 5,935,083 A | 8/1999 | Williams | 6,443,887 B1 | 9/2002 | Derus et al. |
| 5,938,669 A | 8/1999 | Klaiber et al. | 6,443,893 B1 | 9/2002 | Schnakenberg et al. |
| 5,951,487 A | 9/1999 | Brehmeier-Flick et al. | 6,450,173 B1 | 9/2002 | Forsell |
| 5,957,861 A | 9/1999 | Combs et al. | 6,450,543 B1 | 9/2002 | Fukano et al. |

| Patent No. | Date | Name |
|---|---|---|
| 6,450,946 B1 | 9/2002 | Forsell |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell et al. |
| 6,460,543 B1 | 10/2002 | Forsell |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell |
| 6,464,628 B1 | 10/2002 | Forsell |
| 6,470,212 B1 | 10/2002 | Weijand et al. |
| 6,470,213 B1 | 10/2002 | Alley |
| 6,470,892 B1 | 10/2002 | Forsell |
| 6,471,635 B1 | 10/2002 | Forsell |
| 6,475,136 B1 | 11/2002 | Forsell |
| 6,475,170 B1 | 11/2002 | Doron et al. |
| 6,481,292 B1 | 11/2002 | Reich |
| 6,482,145 B1 | 11/2002 | Forsell |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,503,208 B1 | 1/2003 | Skovlund et al. |
| 6,504,286 B1 | 1/2003 | Porat et al. |
| 6,505,062 B1 | 1/2003 | Ritter et al. |
| 6,511,490 B2 | 1/2003 | Robert |
| 6,516,212 B1 | 2/2003 | Bladen et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,587,709 B2 | 7/2003 | Solf et al. |
| 6,589,189 B2 | 7/2003 | Meyerson et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,654,629 B2 | 11/2003 | Montegrande |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers |
| 6,689,046 B2 | 2/2004 | Sayet et al. |
| 6,690,963 B2 | 2/2004 | Ben-Haim et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,757,557 B1 | 6/2004 | Bladen et al. |
| 6,779,851 B2 | 8/2004 | Bouchiere |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaeft et al. |
| 6,890,300 B2 | 5/2005 | Lloyd et al. |
| 6,896,651 B2 | 5/2005 | Gross et al. |
| 6,898,690 B2 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,143,462 B2 | 12/2006 | Hohlbein |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Makek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1* | 8/2001 | Forsell ............... 128/899 |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0023134 A1 | 1/2003 | Tracey |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0120150 A1 | 6/2003 | Govari |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2003/0225371 A1 | 12/2003 | Hadzic et al. |
| 2004/0014456 A1 | 1/2004 | Vnnen |
| 2004/0039256 A1 | 2/2004 | Kawatahara et al. |
| 2004/0054351 A1 | 3/2004 | Deniega et al. |
| 2004/0054352 A1 | 3/2004 | Clark et al. |
| 2004/0055610 A1 | 3/2004 | Forsell |
| 2004/0064030 A1 | 4/2004 | Forsell |
| 2004/0082867 A1 | 4/2004 | Esch et al. |
| 2004/0082904 A1 | 4/2004 | Houde et al. |
| 2004/0106874 A1 | 6/2004 | Eigler et al. |
| 2004/0113790 A1 | 6/2004 | Hamel et al. |
| 2004/0133092 A1 | 7/2004 | Kain |
| 2004/0143212 A1 | 7/2004 | Trombley et al. |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0193045 A1 | 9/2004 | Scarborough et al. |
| 2004/0215159 A1 | 10/2004 | Forsell |
| 2004/0243148 A1 | 12/2004 | Wasielewski |
| 2004/0254537 A1 | 12/2004 | Conlon et al. |
| 2005/0004516 A1 | 1/2005 | Vanney |
| 2005/0015014 A1 | 1/2005 | Fonseca et al. |
| 2005/0025979 A1 | 2/2005 | Sandt et al. |

| | | |
|---|---|---|
| 2005/0027175 A1 | 2/2005 | Yang |
| 2005/0027998 A1 | 2/2005 | Teglia et al. |
| 2005/0038328 A1 | 2/2005 | Stoehrer et al. |
| 2005/0061079 A1 | 3/2005 | Schulman |
| 2005/0065450 A1 | 3/2005 | Stuebe et al. |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0203360 A1 | 9/2005 | Brauker et al. |
| 2005/0240144 A1 | 10/2005 | Wassermann et al. |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler, Jr. et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0089619 A1 | 4/2006 | Ginggen |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0118793 A1 | 6/2006 | Yang et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149161 A1 | 7/2006 | Wilson et al. |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |
| 2008/0172072 A1 | 7/2008 | Pool et al. |
| 2008/0250340 A1 | 10/2008 | Dlugos et al. |
| 2008/0250341 A1 | 10/2008 | Dlugos et al. |
| 2009/0005703 A1 | 1/2009 | Fasciano |

FOREIGN PATENT DOCUMENTS

| | | |
|---|---|---|
| CA | 1059035 | 7/1979 |
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1119469 | 3/1982 |
| CN | 1059035 | 2/1992 |
| CN | 1241003 | 1/2000 |
| DE | 9416395 | 12/1994 |
| DE | 10156494 | 6/2003 |
| EP | 0417171 | 3/1991 |
| EP | 0508141 | 10/1992 |
| EP | 0568730 | 11/1993 |
| EP | 0605302 | 7/1994 |
| EP | 0 654 232 | 5/1995 |
| EP | 0660482 | 6/1995 |
| EP | 0714017 | 5/1996 |
| EP | 0769340 | 4/1997 |
| EP | 0846475 | 6/1998 |
| EP | 0848780 | 6/1998 |
| EP | 0876808 | 11/1998 |
| EP | 0888079 | 1/1999 |
| EP | 0914059 | 5/1999 |
| EP | 0981293 | 3/2000 |
| EP | 0997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 4581 | 6/2004 |
| EP | 1442715 | 8/2004 |
| EP | 1488735 | 12/2004 |
| EP | 1500411 | 1/2005 |
| EP | 1510306 | 3/2005 |
| EP | 1518514 | 3/2005 |

| | | |
|---|---|---|
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1600120 | 11/2005 |
| EP | 1609440 | 12/2005 |
| EP | 1649884 | 4/2006 |
| EP | 1674033 | 6/2006 |
| EP | 1 676 527 | 7/2006 |
| EP | 1676527 | 7/2006 |
| EP | 1736123 | 12/2006 |
| EP | 1799119 | 6/2007 |
| GB | 2355937 | 5/2001 |
| JP | 2006/175191 | 7/2006 |
| WO | WO 89/11244 | 11/1989 |
| WO | WO 89/11701 | 11/1989 |
| WO | WO 90/04368 | 5/1990 |
| WO | WO 95/11057 | 4/1995 |
| WO | WO 97/15351 | 5/1997 |
| WO | WO 97/33513 | 9/1997 |
| WO | WO 98/33554 | 8/1998 |
| WO | WO 98/35610 | 8/1998 |
| WO | WO 99/01063 | 1/1999 |
| WO | WO 99/18850 | 4/1999 |
| WO | WO 00/04945 | 2/2000 |
| WO | WO 00/33738 | 6/2000 |
| WO | WO 00/72899 | 12/2000 |
| WO | WO 01/04487 | 1/2001 |
| WO | WO 01/12075 | 2/2001 |
| WO | WO 01/12076 | 2/2001 |
| WO | WO 01/12077 | 2/2001 |
| WO | WO 01/12078 | 2/2001 |
| WO | WO 01/21066 | 3/2001 |
| WO | WO 01/36014 | 5/2001 |
| WO | WO 01/45485 | 6/2001 |
| WO | WO 01/45486 | 6/2001 |
| WO | WO 01/47431 | 7/2001 |
| WO | WO 01/47432 | 7/2001 |
| WO | WO 01/47433 | 7/2001 |
| WO | WO 01/47434 | 7/2001 |
| WO | WO 01/47435 | 7/2001 |
| WO | WO 01/47440 | 7/2001 |
| WO | WO 01/47575 | 7/2001 |
| WO | WO 01/48451 | 7/2001 |
| WO | WO 01/49245 | 7/2001 |
| WO | WO 01/50832 | 7/2001 |
| WO | WO 01/50833 | 7/2001 |
| WO | WO 01/54626 | 8/2001 |
| WO | WO 01/58388 | 8/2001 |
| WO | WO 01/58390 | 8/2001 |
| WO | WO 01/58391 | 8/2001 |
| WO | WO 01/58393 | 8/2001 |
| WO | WO 01 60453 | 8/2001 |
| WO | WO 01/81890 | 11/2001 |
| WO | WO 02/00118 | 1/2002 |
| WO | WO 02/15769 | 2/2002 |
| WO | WO 02/26161 | 4/2002 |
| WO | WO 02/053228 | 7/2002 |
| WO | WO 02/055126 | 7/2002 |
| WO | WO 02/058551 | 8/2002 |
| WO | WO 02/065894 | 8/2002 |
| WO | WO 02/076289 | 10/2002 |
| WO | WO 02/082984 | 10/2002 |
| WO | WO 02/089655 | 11/2002 |
| WO | WO 02/090894 | 11/2002 |
| WO | WO 03/002192 | 1/2003 |
| WO | WO 03/002193 | 1/2003 |
| WO | WO 03/061467 | 1/2003 |
| WO | WO 03/020182 | 3/2003 |
| WO | WO 03/043534 | 5/2003 |
| WO | WO 03/061504 | 7/2003 |
| WO | WO 03/096889 | 11/2003 |
| WO | WO 2004/014245 | 2/2004 |
| WO | WO 2004/014456 | 2/2004 |
| WO | WO 2004/019773 | 3/2004 |
| WO | WO 2004/030541 | 4/2004 |
| WO | WO 2004/058101 | 7/2004 |
| WO | WO 2004/066879 | 8/2004 |
| WO | WO 2004/110263 | 12/2004 |
| WO | WO 2005/000206 | 1/2005 |
| WO | WO 2005/007075 | 1/2005 |
| WO | WO 2005/027998 | 3/2005 |
| WO | WO 2005/084544 | 9/2005 |
| WO | WO 2005/107583 | 11/2005 |
| WO | WO 2006/001851 | 1/2006 |
| WO | WO 2006/018927 | 2/2006 |
| WO | WO 2006/035446 | 4/2006 |
| WO | WO 2006/113187 | 10/2006 |
| WO | WO 2006/122285 | 11/2006 |
| WO | WO 2007/067206 | 6/2007 |
| WO | WO 2007/070906 | 6/2007 |
| WO | WO 2007/072452 | 6/2007 |
| WO | WO 2007/081304 | 7/2007 |
| WO | WO 2007/104356 | 9/2007 |
| WO | WO20 07/140430 | 12/2007 |
| WO | WO 2007/140430 | 12/2007 |
| WO | WO 2008/088949 | 7/2008 |

OTHER PUBLICATIONS

Author Unknown—"Report—Wireless in Healthcare"—The FocalPoint Group—2004.
U.S. Appl. No. 12/039,014, filed Feb. 28, 2008, Dlugos, Jr. et al.
EP Search Report dated Sep. 28, 2006 for Application No. 06253286.
EP Search Report dated Jun. 13, 2007 for Application No. 07250931.
EP Search Report dated Jun. 18, 2007 for Application No. 07250932.
EP Search Report dated May 2, 2008 for Application No. 06250968.
EP Search Report dated Nov. 3, 2008 for Application No. 08251508.
EP Search Report dated Feb. 10, 2009 for Application No. 07250915.
EP Examination Report dated Jul. 23, 2007 for Application No. 06253286.
EP Examination Report dated Dec. 9, 2008 for Application No. 06250968.
Kirchner, G., "Honeywell and Synopsys; Concept-to-Parts Solutions for Next Generation Rad-Hard ASICs," in online magazine Compiler, http://www.synopsys.com/news/pubs/compiler/artlead_redasic-apr05.html,(Apr. 2005), pp. 1-5.
Neukomm, P.A. et al., "Passive Wireless Actuator Control and Sensor Signal Transmission," Sensors and Actuators, A21-A23 (1990) pp. 258-262.
European Search Report dated Oct. 30, 2006 for Application No. 06253276.
European Examination Report dated Jul. 23, 2009 for Application No. 06253286.
European Search Report dated May 2, 2008 for Application No. 06250968.
European Search Report dated Feb. 10, 2009 for Application No. 0725915.
European Search Report dated Jun. 19, 2009 for Application No. 09250581.
European Search Report dated Jul. 10, 2009 for Application No. 09250590.
European Search Report dated Jul. 10, 2009 for Application No. 09250600.
European Search Report dated Aug. 13, 2009 for Application No. 08251093.
International Search Report and Written Opinion dated Sep. 22, 2008 for Application No. PCT/US2008/053394.
Abstract for JP 2006/175191.

* cited by examiner

MONITORING OF A FOOD INTAKE RESTRICTION DEVICE

PRIORITY

This application is a continuation-in-part of prior co-pending U.S. Non-Provisional application Ser. No. 11/167,861, filed Jun. 24, 2005, entitled "Remote Monitoring and Adjustment of Food Intake Restriction Device," the disclosure of which is incorporated by reference herein. This application is also a continuation-in-part of prior U.S. Non-Provisional application Ser. No. 11/065,410, filed Feb. 24, 2005, now U.S. Pat. No. 7,699,770 entitled "Device for Non-Invasive Measurement of Fluid Pressure in an Adjustable Restriction Device," the disclosure of which is incorporated by reference herein.

FIELD

Embodiments of the present invention relate generally to an implanted restrictive opening device and, more particularly, to a communication system for monitoring physiological parameters related to an implanted food intake restriction device.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device" which issued on May 30, 2000, which is incorporated herein by reference. To the extent that an adjustable gastric band system is fluid based, those of ordinary skill in the art will appreciate that it may be advantageous to acquire data indicating the pressure of fluid in the band system. Similar advantages may be achieved with fluid-filled members implanted within the stomach cavity or elsewhere. Such pressure data may be obtained before, during, and/or after pressure adjustment, and may be useful for adjustment, diagnostic, monitoring, or other purposes. It may be further advantageous to store such pressure data and/or communicate it to a remote location. The foregoing examples are merely illustrative and not exhaustive. While a variety of techniques and devices have been used treat obesity, it is believed that no one prior to the inventors has previously made or used an invention as described in the appended claims.

SUMMARY

In one aspect, a system for obtaining data from an implanted device comprises an implantable restriction forming device. The implantable restriction forming device is operable to form a restriction in a patient. The implantable restriction device comprises a fluid. The system further comprises an implantable pressure sensor in communication with the implantable restriction forming device. The implantable pressure sensor is operable to sense the pressure of the fluid. The system further comprises one or more implantable communicators in communication with the implantable pressure sensor. The one or more implantable communicators are operable to communicate data from within a patient. The system further comprises one or more external communicators in communication with the one or more implantable communicators. The one or more external communicators are operable to externally receive data communicated from within the patient by the one or more implantable communicators. The system further comprises a storage device in communication with the one or more external communicators. The storage device is operable to store at least a portion of data received by the one or more external communicators.

In another aspect, a system for obtaining data from an implanted device comprises a TET communicator that is operable to provide power to a device implanted within a patient. The system further comprises a telemetry communicator that is operable to transmit data communicated from one or more implantable pressure sensors located within a patient. The system further comprises a power supply in communication with the TET communicator. The power supply is operable to provide power to the TET communicator. The system further comprises a storage device in communication with the telemetry communicator. The storage device is operable to store data transmitted from the telemetry communicator. The system further comprises a communication port in communication with the storage device. The communication port is configured to communicate data from the storage device to one or both of a docking station or a network. The system further comprises a microprocessor in communication with the TET communicator, the telemetry communicator, the power supply, the storage device, and the communication port. The microprocessor is configured to regulate power supplied by the power supply to the TET communicator. The microprocessor is further configured to regulate transmission of data from the telemetry communicator to the storage device. The microprocessor is further configured to regulate transmission of data from the storage device to the communication port.

In yet another aspect, a method of obtaining data from an implanted device comprises receiving pressure data indicating pressure of fluid in an implanted restriction device. The implanted restriction device is operable to form a restriction in a patient. The pressure data is obtained using a pressure sensor in communication with the implanted restriction device. The pressure data is received using a communicator positioned locally relative to the patient. The method further comprises storing the received pressure data obtained using the communicator. The received pressure data is stored in a storage device positioned locally relative to the patient. The method further comprises transmitting at least a portion of the stored pressure data to a remote location. The remote location is positioned remotely relative to the patient. The method further comprises receiving the transmitted pressure data at the remote location and evaluating the pressure data received at the remote location.

Still other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
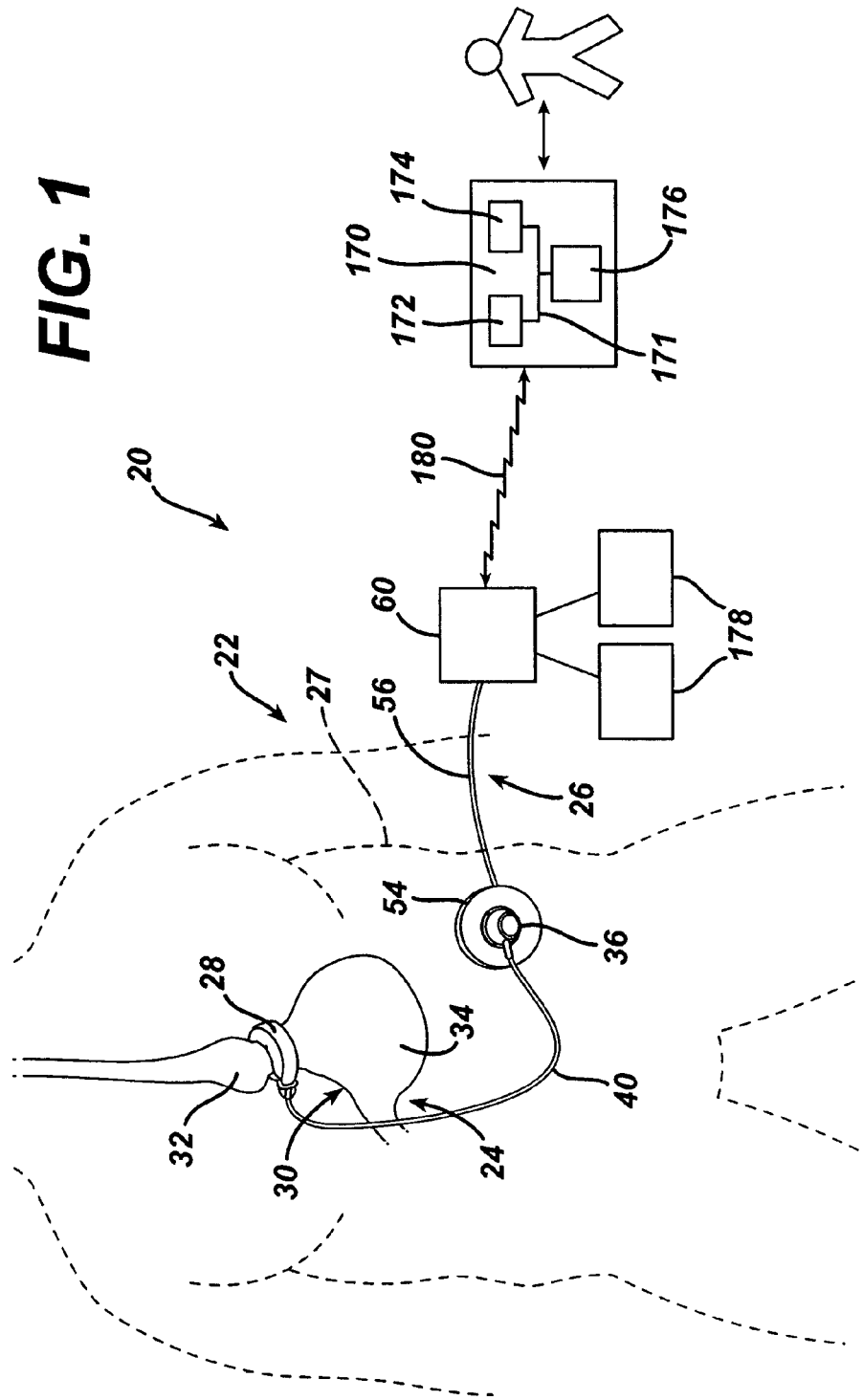
FIG. 1 is a simplified, schematic diagram of an implanted restrictive opening device and a bi-directional communication system between the implanted device and a remote monitoring unit.

Referring now to the drawings in detail, wherein like numerals indicate the same elements throughout the views, FIG. 1 provides a simplified, schematic diagram of a bi-directional communication system 20 for transmitting data between an implanted restrictive opening device and a remotely located monitoring unit. Through communication system 20, data and command signals may be transmitted between the implanted device and a remotely located physician for monitoring and affecting patient treatment. The communication system of the invention enables a physician to control the restrictive opening device and monitor treatment without meeting face-to-face with the patient. For purposes of the disclosure herein, the terms "remote" and "remotely located" are defined as being at a distance of greater than six feet. In FIG. 1 and the following disclosure, the restrictive opening device is shown and described as being a food intake restriction device 22 for use in bariatric treatment. The use of a food intake restriction device is only representative however, and the present invention may be utilized with other types of implanted restrictive opening devices without departing from the scope of the invention.

As shown in FIG. 1, a first portion 24 of intake restriction device 22 is implanted beneath a patient's skin 27, while a second portion 26 is located external to the patient's skin. Implanted portion 24 comprises an adjustable restriction band 28 that is implanted about the gastrointestinal tract for the treatment of morbid obesity. In this application, adjustable band 28 is looped about the outer wall of a stomach 30 to create a stoma between an upper pouch 32 and a lower pouch 34 of the stomach. Adjustable band 28 may include a cavity made of silicone rubber, or another type of biocompatible material, that inflates inwardly against stomach 30 when filled with a fluid. Alternatively, band 28 may comprise a mechanically adjustable device having a fluid cavity that experiences pressure changes with band adjustments, or a combination hydraulic/mechanical adjustable band.

An injection port 36, which will be described in greater detail below, is implanted in a body region accessible for needle injections and telemetry communication signals. In the embodiment shown, injection port 36 fluidly communicates with adjustable band 28 via a catheter 40. A surgeon may position and permanently implant injection port 36 inside the body of the patient in order to perform adjustments of the food intake restriction or stoma. Injection port 36 is typically implanted in the lateral, subcostal region of the patient's abdomen under the skin and layers of fatty tissue. Alternatively, the surgeon may implant injection port 36 on the sternum of the patient.

Figure 2:
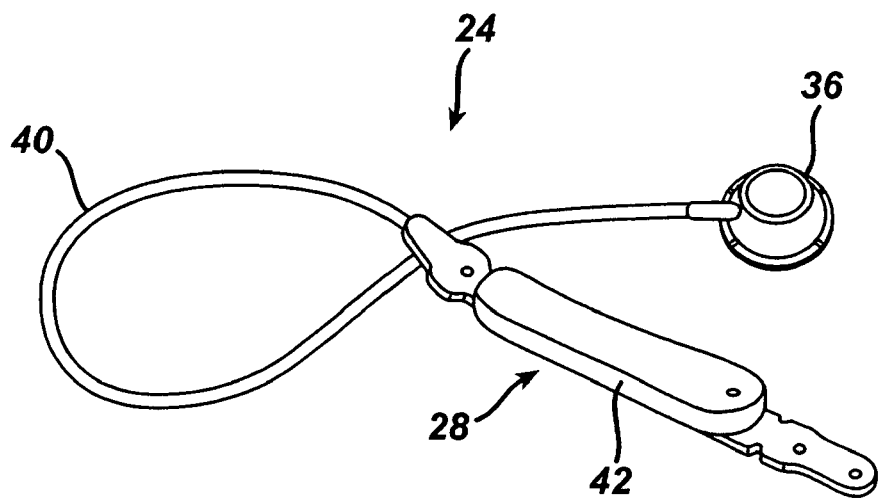
FIG. 2 is a more detailed, perspective view of an implantable portion of the food intake restriction device shown in FIG. 1.

FIG. 2 illustrates adjustable band 28 in greater detail. In this embodiment, band 28 includes a variable volume cavity 42 that expands or contracts against the outer wall of the stomach to form an adjustable stoma for controllably restricting food intake into the stomach. A physician may decrease the size of the stoma opening by adding fluid to variable volume cavity 42 or, alternatively, may increase the stoma size by withdrawing fluid from the cavity. Fluid may be added or withdrawn by inserting a needle into injection port 36. The fluid may be, but is not restricted to, a 0.9 percent saline solution.

Returning now to FIG. 1, external portion 26 of intake restriction device 22 comprises a hand-held antenna 54 electrically connected (in this embodiment via an electrical cable assembly 56) to a local unit 60. Electrical cable assembly 56 may be detachably connected to local unit 60 or antenna 54 to facilitate cleaning, maintenance, usage, and storage of external portion 26. Local unit 60 is a microprocessor-controlled device that communicates with implanted device 22 and a remote unit 170, as will be described further below. Through antenna 54, local unit 60 non-invasively communicates with implanted injection port 36. Antenna 54 may be held against the patient's skin near the location of injection port 36 to transmit telemetry and power signals to injection port 36.

Figure 3:
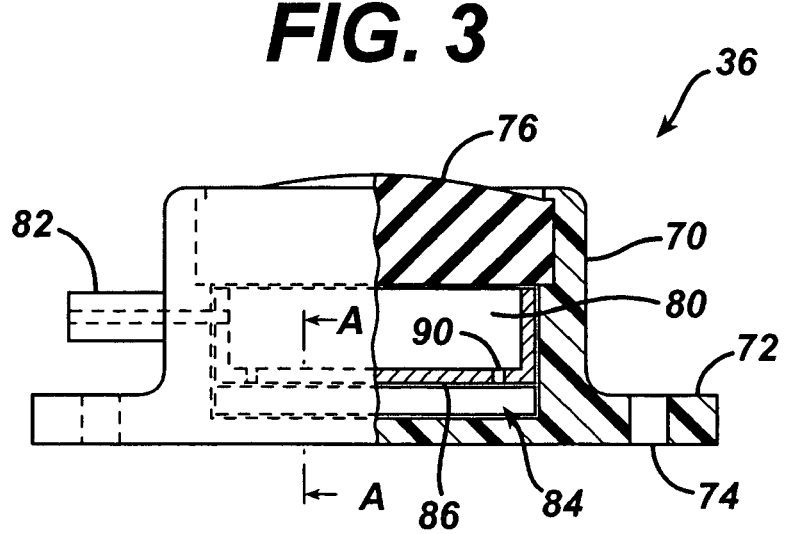
FIG. 3 is a side, partially sectioned view of the injection port shown in FIG. 2.

Turning now to FIG. 3, which depicts a side, partially sectioned view of an exemplary injection port 36. As shown in FIG. 3, injection port 36 comprises a rigid housing 70 having an annular flange 72 containing a plurality of attachment holes 74 for fastening the injection port to tissue in a patient. A surgeon may attach injection port 36 to the tissue, such as the fascia covering an abdominal muscle, using any one of numerous surgical fasteners including suture filaments, staples, and clips. Injection port 36 further comprises a septum 76 typically made of a silicone rubber and compressively retained in housing 70. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 36. Injection port 36 further comprises a reservoir 80 for retaining the fluid and a catheter connector 82. Connector 82 attaches to catheter 40, shown in FIG. 2, to form a closed hydraulic circuit between reservoir 80 and cavity 42. Housing 70 and connector 82 may be integrally molded from a biocompatible polymer or constructed from a metal such as titanium or stainless steel.

Injection port 36 also comprises a pressure sensor 84 for measuring fluid pressure within the device. The pressure measured by sensor 84 corresponds to the amount of restriction applied by band 28 to the patient's stomach or other body cavity. The pressure measurement is transmitted from sensor 84 to local unit 60 via telemetry signals using antenna 54. Local unit 60 may display, print and/or transmit the pressure measurement to a remote monitoring unit for evaluation, as will be described in more detail below. In the embodiment shown in FIG. 3, pressure sensor 84 is positioned at the bottom of fluid reservoir 80 within housing 70. A retaining cover 86 extends above pressure sensor 84 to substantially separate the sensor surface from reservoir 80, and protect the sensor from needle penetration. Retaining cover 86 may be made of a ceramic material such as, for example, alumina, which resists needle penetration yet does not interfere with electronic communications between pressure sensor 84 and antenna 54. Retaining cover 86 includes a vent 90 that allows fluid inside of reservoir 80 to flow to and impact upon the surface of pressure sensor 84.

Figure 4:
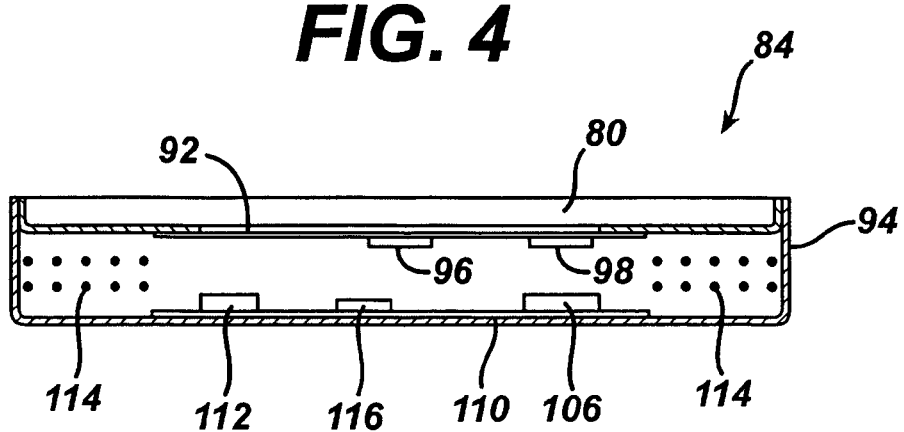
FIG. 4 is a side, sectional view, taken along line A-A of FIG. 3, illustrating an exemplary pressure sensor for measuring fluid pressure in the intake restriction device of FIG. 2.

FIG. 4 is a side, sectional view of pressure sensor 84, taken along line A-A of FIG. 3, illustrating an exemplary embodiment for measuring fluid pressure. Pressure sensor 84 is hermetically sealed within a housing 94 to prevent fluid infiltrating and effecting the operation of the sensor. The exterior of pressure sensor 84 includes a diaphragm 92 having a deformable surface. Diaphragm 92 is formed by thinning out a section of the bottom of titanium reservoir 80 to a thickness between 0.001" and 0.002". As fluid flows through vent 90 in reservoir 80, the fluid impacts upon the surface of diaphragm 92, causing the surface to mechanically displace. The mechanical displacement of diaphragm 92 is converted to an electrical signal by a pair of variable resistance, silicon strain gauges 96, 98. Strain gauges 96, 98 are attached to diaphragm 92 on the side opposite the working fluid in reservoir 80. Strain gauge 96 is attached to a center portion of diaphragm 92 to measure the displacement of the diaphragm. The second, matched strain gauge 98 is attached near the outer edge of diaphragm 92. Strain gauges 96, 98 may be attached to diaphragm 92 by adhesives, or may be diffused into the diaphragm structure. As fluid pressure within band 28 fluctuates, the surface of diaphragm 92 deforms up or down at the bottom of reservoir 80. The deformation of diaphragm 92 produces a resistance change in the center strain gauge 96.

Figure 5:
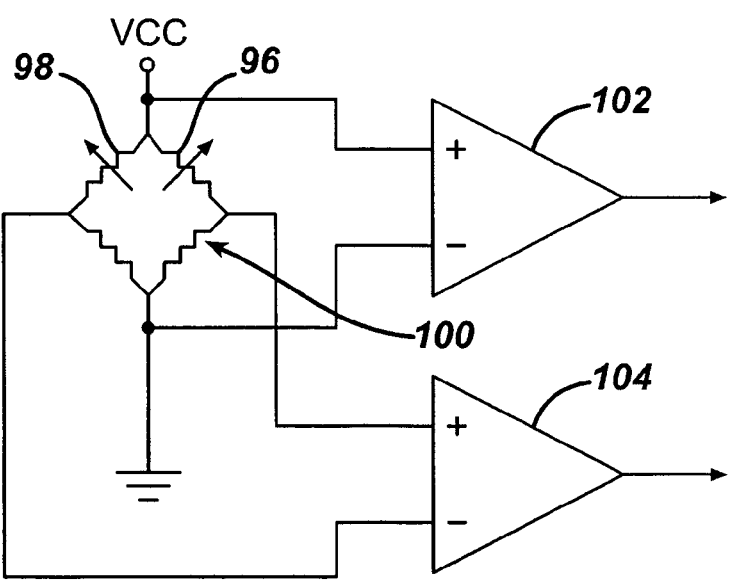
FIG. 5 is a simplified schematic of a variable resistance circuit for the pressure sensor shown in FIG. 4.

As shown in FIG. 5, strain gauges 96, 98 form the top two resistance elements of a half-compensated, Wheatstone bridge circuit 100. As strain gauge 96 reacts to the mechanical displacements of diaphragm 92, the changing resistance of the gauge changes the potential across the top portion of the bridge circuit. Strain gauge 98 is matched to strain gauge 96 and athermalizes the Wheatstone bridge circuit. Differential amplifiers 102, 104 are connected to bridge circuit 100 to measure the change in potential within the bridge circuit due to the variable resistance strain gauges. In particular, differential amplifier 102 measures the voltage across the entire bridge circuit, while differential amplifier 104 measures the differential voltage across the strain gauge half of bridge circuit 100. The greater the differential between the strain gauge voltages, for a fixed voltage across the bridge, the greater the pressure difference. If desired, a fully compensated Wheatstone bridge circuit could also be used to increase the sensitivity and accuracy of the pressure sensor 84. In a fully compensated bridge circuit, four strain gauges are attached to the surface of diaphragm 92, rather than only two strain gauges as shown in FIG. 4.

Returning to FIG. 4, the output signals from differential amplifiers 102, 104 are applied to a microcontroller 106. Microcontroller 106 is integrated into a circuit board 110 within housing 94. A temperature sensor 112 measures the temperature within injection port 36 and inputs a temperature signal to microcontroller 106. Microcontroller 106 uses the temperature signal from sensor 112 to compensate for variations in body temperature and residual temperature errors not accounted for by strain gauge 98. Compensating the pressure measurement signal for variations in body temperature increases the accuracy of the pressure sensor 84. Additionally, a TET/telemetry coil 114 is located within housing 94. Coil 114 is connected to a capacitor 116 to form a tuned tank circuit for receiving power from and transmitting physiological data, including the measured fluid pressure, to local unit 60. FIGS. 3-5 illustrate one exemplary embodiment for measuring fluid pressure within an intake restriction device. Additional embodiments for measuring fluid pressure are described in U.S. patent application Ser. No. 11/065,410 entitled "Non-invasive Measurement of Fluid Pressure in a Bariatric Device," the disclosure of which is incorporated herein by reference.

Figure 6:
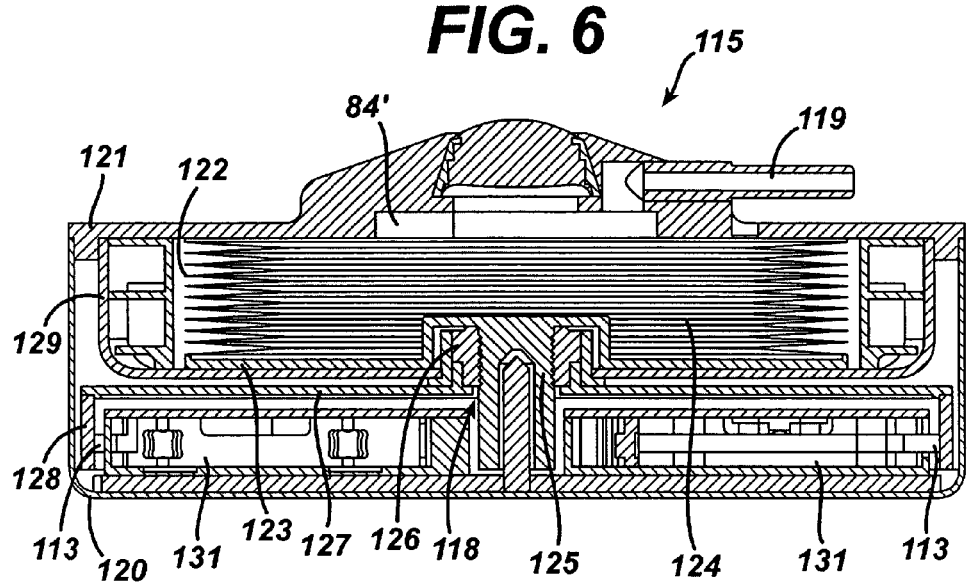
FIG. 6 is a cross-sectional view of an alternative bi-directional infuser for the food intake restriction device of FIG. 2.

As an alternative to injection port 36, implanted portion 24 may include a bi-directional infuser for varying the fluid level within the adjustable restriction band 28. With an infuser, fluid can be added or withdrawn from band 28 via telemetry command signals, without the need to insert a syringe through the patient's skin and into the port septum. FIG. 6 is a cross-sectional view of an exemplary infuser 115. As shown in FIG. 6, infuser 115 includes a pump, designated generally as 118, for non-invasively transferring fluid into or out of the band in response to telemetry command signals. Pump 118 is encased within a cylindrical outer housing 120 having an annular cover 121 extending across a top portion. A collapsible bellows 122 is securely attached at a top peripheral edge to cover 121. Bellows 122 is comprised of a suitable material, such as titanium, which is capable of repeated flexure at the folds of the bellows, but which is sufficiently rigid so as to be non-compliant to variations in pressure. A lower peripheral edge of bellows 122 is secured to an annular bellows cap 123, which translates vertically within pump 118. The combination of cover 121, bellows 122 and bellows cap 123 defines the volume of a fluid reservoir 124. A catheter connector 119 attaches to catheter 40 (shown in FIG. 2) to form a closed hydraulic circuit between the band and fluid reservoir 124. The volume in reservoir 124 may be expanded by moving bellows cap 123 in a downward direction, away from cover 121. As bellows cap 123 descends, the folds of bellows 122 are stretched, creating a vacuum to pull fluid from the band, through catheter 40 and connector 119, and into reservoir 124. Similarly, the volume in reservoir 124 may be decreased by moving bellows cap 123 in an upward direction towards cover 121, thereby compressing the folds of bellows 122 and forcing fluid from the reservoir through catheter 40 and connector 119 and into band 28.

Bellows cap 123 includes an integrally formed lead screw portion 125 that operatively engages a matching thread on a cylindrical nut 126. The outer circumference of nut 126 is securely attached to an axial bore of a rotary drive plate 127. A cylindrical drive ring 128 is in turn mounted about the outer annular edge of rotary drive plate 127. Nut 126, drive plate 127 and drive ring 128 are all securely attached together by any suitable means to form an assembly that rotates as a unit about an axis formed by screw portion 125. A bushing frame 129 encloses TET and telemetry coils (not shown) for transmitting power and data signals between antenna 54 and pump 118.

Drive ring 128 is rotatably driven by one or more piezoelectric harmonic motors. In the embodiment shown in FIG. 6, two harmonic motors 131 are positioned so that a tip 113 of each motor is in frictional contact with the inner circumference of drive ring 128. When motors 131 are energized, tips 113 vibrate against drive ring 128, producing a "walking" motion along the inner circumference of the ring that rotates the ring. A microcontroller (not shown) in pump 118 is electrically connected to the TET and telemetry coils for receiving power to drive motors 131, as well as receiving and transmitting data signals for the pump. To alter the fluid level in band cavity 42, an adjustment prescription is transmitted by telemetry from antenna 54. The telemetry coil in infuser 115 detects and transmits the prescription signal to the microcontroller. The microcontroller in turn drives motors 131 an appropriate amount to collapse or expand bellows 122 and drive the desired amount of fluid to/from band 28.

In order to measure pressure variations within infuser 115, and, thus, the size of the stoma opening, a pressure sensor, indicated by block 84', is included within bellows 122. Pressure sensor 84' is similar to pressure sensor 84 described above. As the pressure against band 28 varies due to, for example, peristaltic pressure from swallowing, the fluid in band 28 experiences pressure changes. These pressure changes are conveyed back through the fluid in catheter 40 to bellows 122. The diaphragm in pressure sensor 84' deflects in response to the fluid pressure changes within bellows 122. The diaphragm deflections are converted into an electrical signal indicative of the applied pressure in the manner described above with respect to FIGS. 4 and 5. The pressure signal is input to the infuser microcontroller, which transmits the pressure to a monitoring unit external to the patient via the telemetry coil. Additional details regarding the operation of bi-directional infuser 115 may be found in commonly-assigned, co-pending U.S. patent application Ser. No. 11/065,410 entitled "Non-invasive Measurement of Fluid Pressure in a Bariatric Device" which has been incorporated herein by reference.

Figure 7A:
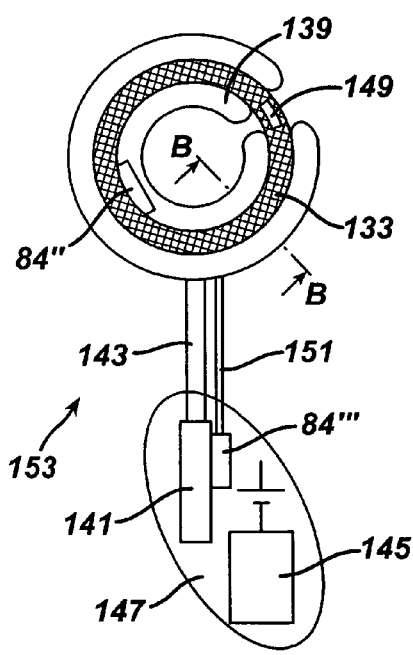
FIG. 7A is a schematic diagram of a mechanically adjustable restriction device incorporating a pressure transducer.
Figure 7B:
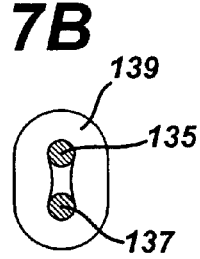
FIG. 7B is a cross-sectional view of the mechanically adjustable device of FIG. 7A taken along line B-B.

FIGS. 7A and 7B depict a mechanically adjustable band 153 for creating a food intake restriction in the abdomen of a patient. Mechanical band 153 may be used as an alternative to hydraulically adjustable band 28 for creating a stoma. Mechanically adjustable band 153 comprises a substantially circular resilient core 133 having overlapping end portions 135, 137. Core 133 is substantially enclosed in a fluid-filled compliant housing 139. A releasable and lockable joint 149 of core 133 protrudes from the ends of housing 139 to enable the core and housing to be placed around the esophagus or stomach of a patient to form a stoma. An implanted motor 141 is spaced from core 133 to mechanically adjust the overlap of the core end portions 135, 137 and, accordingly, the stoma size formed by the core. Motor 141 adjusts the size of core 133 through a drive shaft 143 that is connected to a drive wheel (not shown) within housing 139. Motor 141 is molded together with a remote-controlled power supply unit 145 in a body 147 comprised of silicon rubber, or another similar material.

As motor 141 changes the size of core 133, the pressure of the fluid within housing 139 varies. To measure the pressure variations, a pressure sensor, similar to that described above, is placed in communication with the fluid of housing 139. The pressure sensor may be placed within housing 139, as shown by block 84", so that the pressure variations within the stoma opening are transferred through the fluid in housing 139 to the diaphragm of the sensor. Sensor 84" translates the deflections of the diaphragm into a pressure measurement signal, which is transmitted to an external unit via telemetry in the manner described above. In an alternative scenario, the pressure sensor may be placed within the implanted motor body 147, as indicated by block 84', and fluidly connected to housing 139 via a tube 151 extending alongside drive shaft 143. As fluid pressure varies in housing 139 due to pressure changes within the stoma opening, the pressure differentials are transferred through the fluid in tube 151 to sensor 84'. Sensor 84" generates an electrical signal indicative of the fluid pressure. This signal is transmitted from the patient to an external unit in the manner described above.

Figure 8:
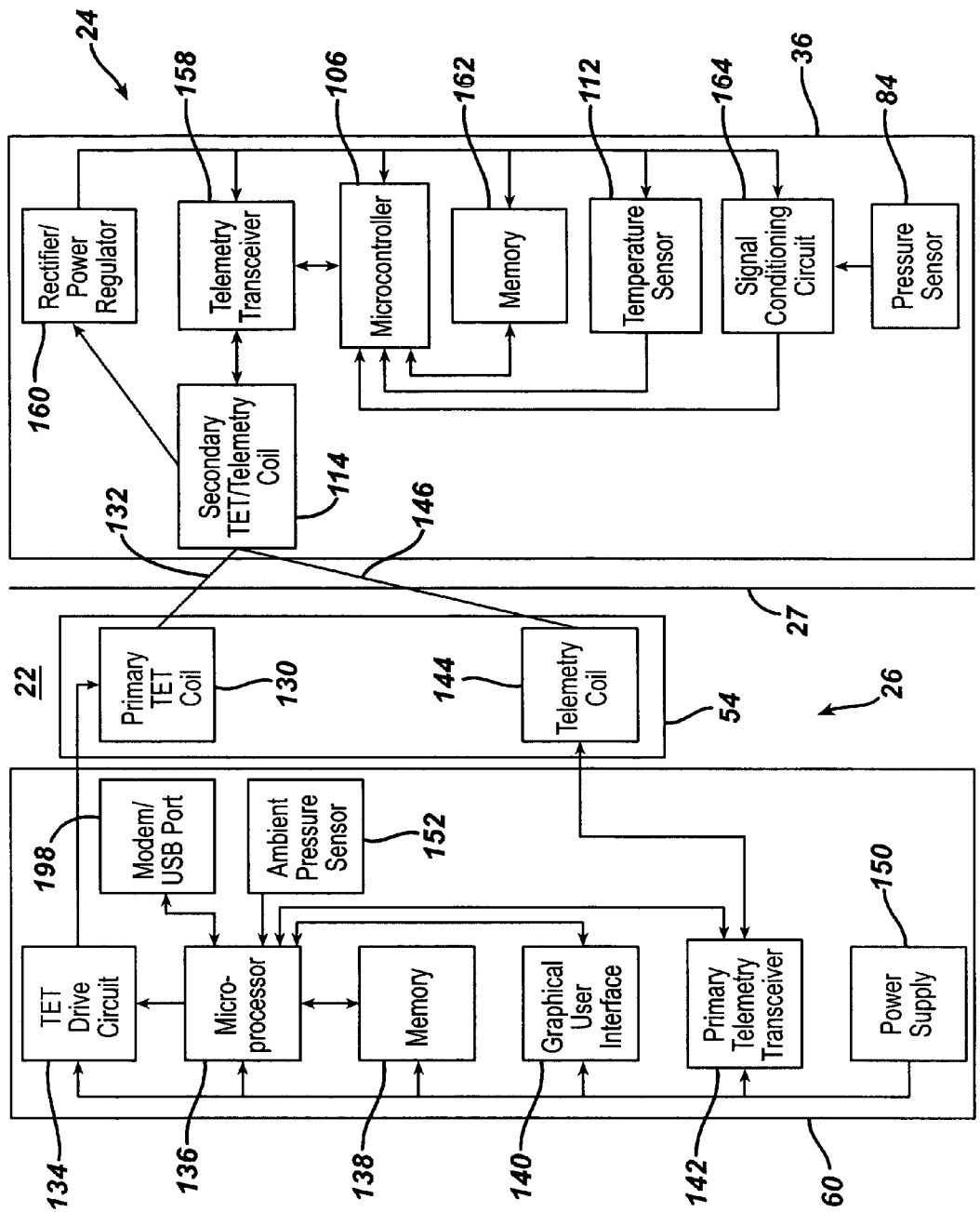
FIG. 8 is a block diagram of the major internal and external components of the intake restriction device shown in FIG. 1.

FIG. 8 is a block diagram illustrating the major components of implanted and external portions 24, 26 of intake restriction device 22. As shown in FIG. 8, external portion 26 includes a primary TET coil 130 for transmitting a power signal 132 to implanted portion 24. A telemetry coil 144 is also included for transmitting data signals to implanted portion 24. Primary TET coil 130 and telemetry coil 144 combine to form antenna 54 as shown. Local unit 60 of external portion 26 includes a TET drive circuit 134 for controlling the application of power to primary TET coil 130. TET drive circuit 134 is controlled by a microprocessor 136. A graphical user interface 140 is connected to microprocessor 136 for inputting patient information and displaying and/or printing data and physician instructions. Through user interface 140, the patient or clinician can transmit an adjustment request to the physician and also enter reasons for the request. Additionally, user interface 140 enables the patient to read and respond to instructions from the physician.

Local unit 60 also includes a primary telemetry transceiver 142 for transmitting interrogation commands to and receiving response data, including sensed fluid pressure, from implanted microcontroller 106. Primary transceiver 142 is electrically connected to microprocessor 136 for inputting and receiving command and data signals. Primary transceiver 142 drives telemetry coil 144 to resonate at a selected RF communication frequency. The resonating circuit generates a downlink alternating magnetic field 146 that transmits command data to implanted microcontroller 106. Alternatively, transceiver 142 may receive telemetry signals transmitted from secondary coil 114. The received data may be stored in a memory 138 associated with microprocessor 136. A power supply 150 supplies energy to local unit 60 in order to power intake restriction device 22. An ambient pressure sensor 152 is connected to microprocessor 136. Microprocessor 136 uses the signal from ambient pressure sensor 152 to adjust the received fluid pressure measurement for variations in atmospheric pressure due to, for example, variations in barometric conditions or altitude.

FIG. 8 also illustrates the major components of implanted portion 24 of device 22.

As shown in FIG. 8, secondary TET/telemetry coil 114 receives power and communication signals from external antenna 54. Coil 114 forms a tuned tank circuit that is inductively coupled with either primary TET coil 130 to power the implant, or primary telemetry coil 144 to receive and transmit data. A telemetry transceiver 158 controls data exchange with coil 114. Additionally, implanted portion 24 includes a rectifier/power regulator 160, microcontroller 106 described above, a memory 162 associated with the microcontroller, temperature sensor 112, pressure sensor 84 and a signal conditioning circuit 164 for amplifying the signal from the pressure sensor. The implanted components transmit the temperature adjusted pressure measurement from sensor 84 to local unit 60 via antenna 54. The pressure measurement may be stored in memory 138 within local unit 60, shown on a display within local unit 60, or transmitted in real time to a remote monitoring station.

As mentioned hereinabove, it is desirable to provide a communication system for the remote monitoring and control of an intake restriction device. Through the communication system, a physician may retrieve a history of fluid pressure measurements from the restriction device to evaluate the efficacy of the bariatric treatment. Additionally, a physician may downlink instructions for a device adjustment. A remotely located clinician may access the adjustment instructions through local unit 60. Using the instructions, the clinician may inject a syringe into injection port 36 and add or remove saline from fluid reservoir 80 to accomplish the device adjustment. Alternatively, the patient may access the instructions through local unit 60, and non-invasively execute the instructions in infuser 115 or mechanically adjustable band 153 using antenna 54. Real-time pressure measurements may be uplinked to the physician during the adjustment for immediate feedback on the effects of the adjustment. Alternatively, the patient or clinician may uplink pressure measurements to the physician after an adjustment for confirmation and evaluation of the adjustment.

As shown in FIG. 1, communication system 20 includes local unit 60 and a remote monitoring unit 170, also referred to herein as a base unit. Remote unit 170 may be located at a physician's office, a hospital or clinic, or elsewhere. Remote unit 170 of the present example is a personal computer type device comprising a microprocessor 172, which may be, for example, an Intel Pentium® microprocessor or the like. Alternatively, remote unit 170 may comprise a dedicated or non-dedicated server that is accessible over a network such as the Internet. In the present example, a system bus 171 interconnects microprocessor 172 with a memory 174 for storing data such as, for example, physiological parameters and patient instructions. A graphical user interface 176 is also interconnected to microprocessor 172 for displaying data and inputting instructions and correspondence to the patient. User interface 176 may comprise a video monitor, a touchscreen, or other display device, as well as a keyboard or stylus for entering information into remote unit 170. Other devices and configurations suitable for providing a remote unit 170 will be apparent to those of ordinary skill in the art.

A number of peripheral devices 178 may interface directly with local unit 60 for inputting physiological data related to the patient's condition. This physiological data may be stored in local unit 60 and uploaded to remote unit 170 during an interrogation or other data exchange. Examples of peripheral devices that can be utilized with the present invention include a weight scale, blood pressure monitor, thermometer, blood glucose monitor, or any other type of device that could be used outside of a physician's office to provide input regarding the current physiological condition of the patient. A weight scale, for example, can electrically communicate with local unit 60 either directly, or wirelessly through antenna 54, to generate a weight loss record for the patient. The weight loss record can be stored in memory 138 of local unit 60. During a subsequent interrogation by remote unit 170, or automatically at prescheduled intervals, the weight loss record can be uploaded by microprocessor 136 to remote unit 170. The weight loss record may be stored in memory 174 of remote unit 170 until accessed by the physician.

Figure 9:
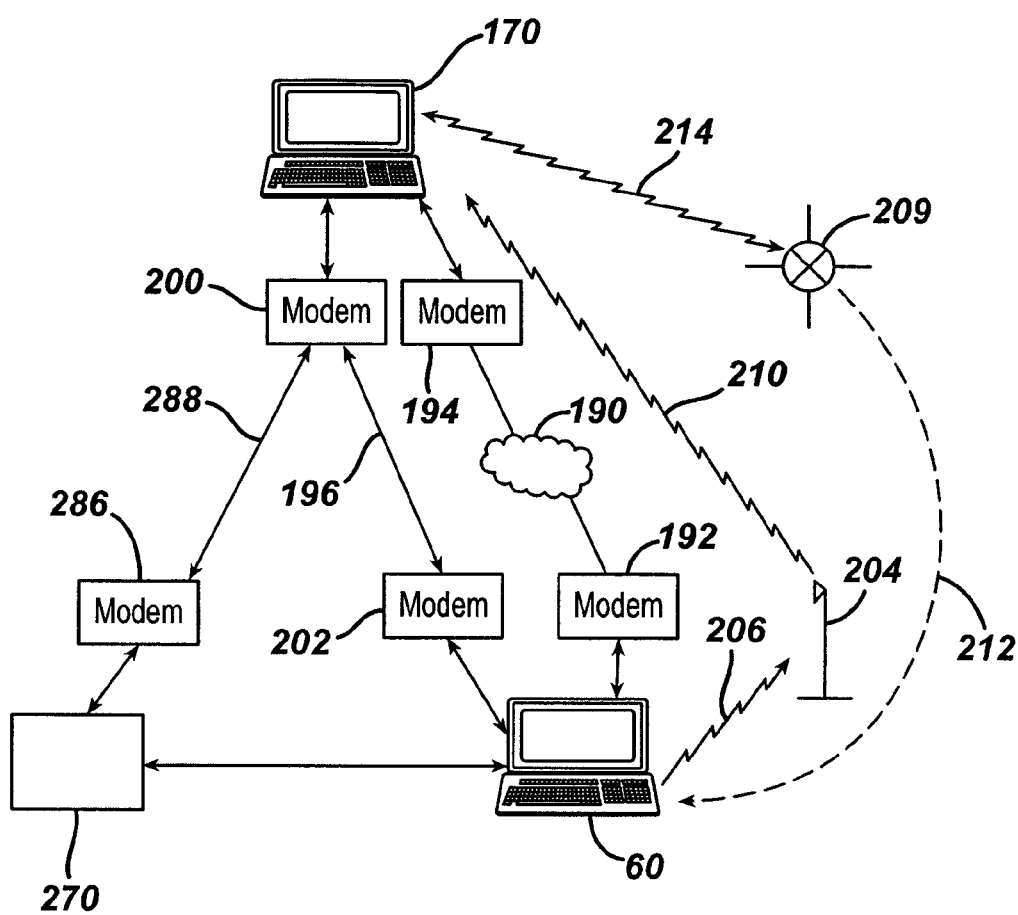
FIG. 9 is a schematic diagram illustrating a number of different communication links between the local and remote units of FIG. 1.

Also as shown in FIG. 1, a communication link 180 is created between local unit 60 and remote unit 170 for transmitting data, including voice, video, instructional information and command signals, between the units. Communication link 180 may comprise any of a broad range of data transmission media including web-based systems utilizing high-speed cable or dial-up connections, public telephone lines, wireless RF networks, satellite, T1 lines or any other type of communication medium suitable for transmitting data between remote locations. FIG. 9 illustrates various media for communication link 180 in greater detail. As shown in FIG. 9, local and remote units 60, 170 may communicate through a number of different direct and wireless connections. In particular, the units may communicate through the Internet 190 using cable or telephone modems 192, 194 or any other suitable device(s). In this instance, data may be transmitted through any suitable Internet communication medium such as, for example, e-mail, instant messaging, web pages, or document transmission. Alternatively, local and remote units 60, 170 may be connected through a public telephone network 196 using modems 200, 202. Units 60, 170 may also communicate through a microwave or RF antenna 204 via tunable frequency waves 206, 210. A communication link may also be established via a satellite 209 and tunable frequency waves 212, 214. In addition to the links described above, it is envisioned that other types of transmission media, that are either known in the art or which may be later developed, could also be utilized to provide the desired data communication between local and remote units 60, 170 without departing from the scope of the invention.

Figure 10:
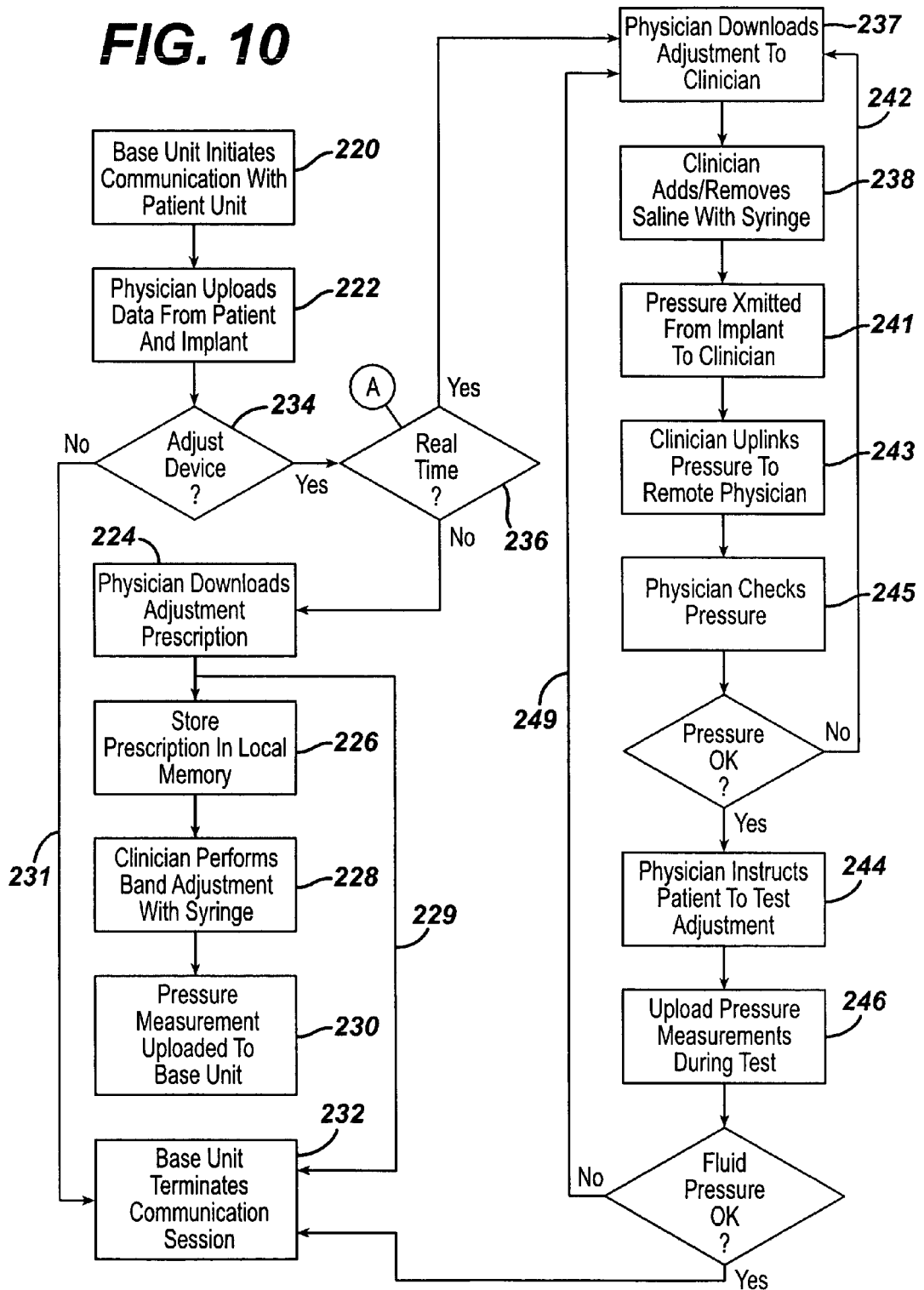
FIG. 10 is a flow diagram of an exemplary communication protocol between the local and remote units for a manually adjustable restriction device.

FIG. 10 is a data flow diagram of an exemplary interaction using bi-directional communication system 20. In this interaction, a physician may download an adjustment prescription that is subsequently manually executed by a clinician present with the patient. A physician initiates the communication session between remote unit 170 and local unit 60 as shown at step 220. The session may be initiated by transmitting an e-mail or instant message via the Internet link 190, or through any of the other communication links described with respect to FIG. 9. During the communication session, the physician may download instructions to memory 138, or may upload previously stored data obtained from device 22 or peripheral devices 178, as shown at step 222. This data may include fluid pressure, a weight history, or a patient compliance report. After the data is uploaded, the physician may evaluate the data and determine the need for a device adjustment, as shown at step 234. If an adjustment is indicated, the physician may download an adjustment prescription command to local unit 60 as shown at step 224. Local unit 60 stores the prescription in memory 138 for subsequent action by a clinician, as shown by step 226. With the patient present, the clinician accesses the prescription from memory 138. The clinician then inserts a syringe into septum 76 of injection port 36 and adds or withdraws the fluid volume specified in the prescription. Following the adjustment, the clinician places antenna 54 over the implant and instructs microcontroller 106 to transmit pressure measurements from sensor 84 to local unit 60. The pressure measurements are uploaded by microprocessor 136 in local unit 60 to remote unit 170, as shown at step 230, to provide a confirmation to the physician that the adjustment instructions were executed, and an indication of the resulting effect on the patient. In an off-line adjustment, the base unit terminates communication with local unit 60 following the downloading of the adjustment prescription, as shown by line 229, or following receipt of the patient data if an adjustment is not indicated, as shown by line 231.

In addition to the off-line adjustment session of steps 220-234, a physician may initiate a real-time interactive adjustment, as indicated at step 236, in order to monitor the patient's condition before, during and after the adjustment. In this instance, the physician downloads an adjustment prescription, as shown at step 237, while the patient is present with a clinician. The clinician inserts a syringe into septum 76 of injection port 36 and adds or withdraws the specified fluid from reservoir 80, as shown at step 238, to execute the prescription. After the injection, the physician instructs the clinician to place antenna 54 over the implant, as shown at step 241, to transmit fluid pressure measurements from the implant to local unit 60. The pressure measurements are then uplinked to the physician through link 180, as shown at step 243. The physician evaluates the pressure measurements at step 245. Based upon the evaluation, the physician may provide further instructions through link 180 to readjust the band as indicated by line 242. Additionally, the physician may provide instructions for the patient to take a particular action, such as eating or drinking, to test the adjustment, as shown at step 244. As the patient performs the test, the physician may upload pressure measurements from the implant, as shown at step 246, to evaluate the peristaltic pressure against the band as the food or liquid attempts to pass through the stoma. If the pressure measurements are too high, indicating a possible obstruction, the physician may immediately transmit additional command signals to the clinician to readjust the band and relieve the obstruction, as indicated by line 249. After the physician is satisfied with the results of the adjustment, the communication session is terminated at step 232. As shown in the flow diagram, communication link 180 enables a physician and patient to interact in a virtual treatment session during which the physician can prescribe adjustments and receive real-time fluid pressure feedback to evaluate the efficacy of the treatment.

Figure 11:
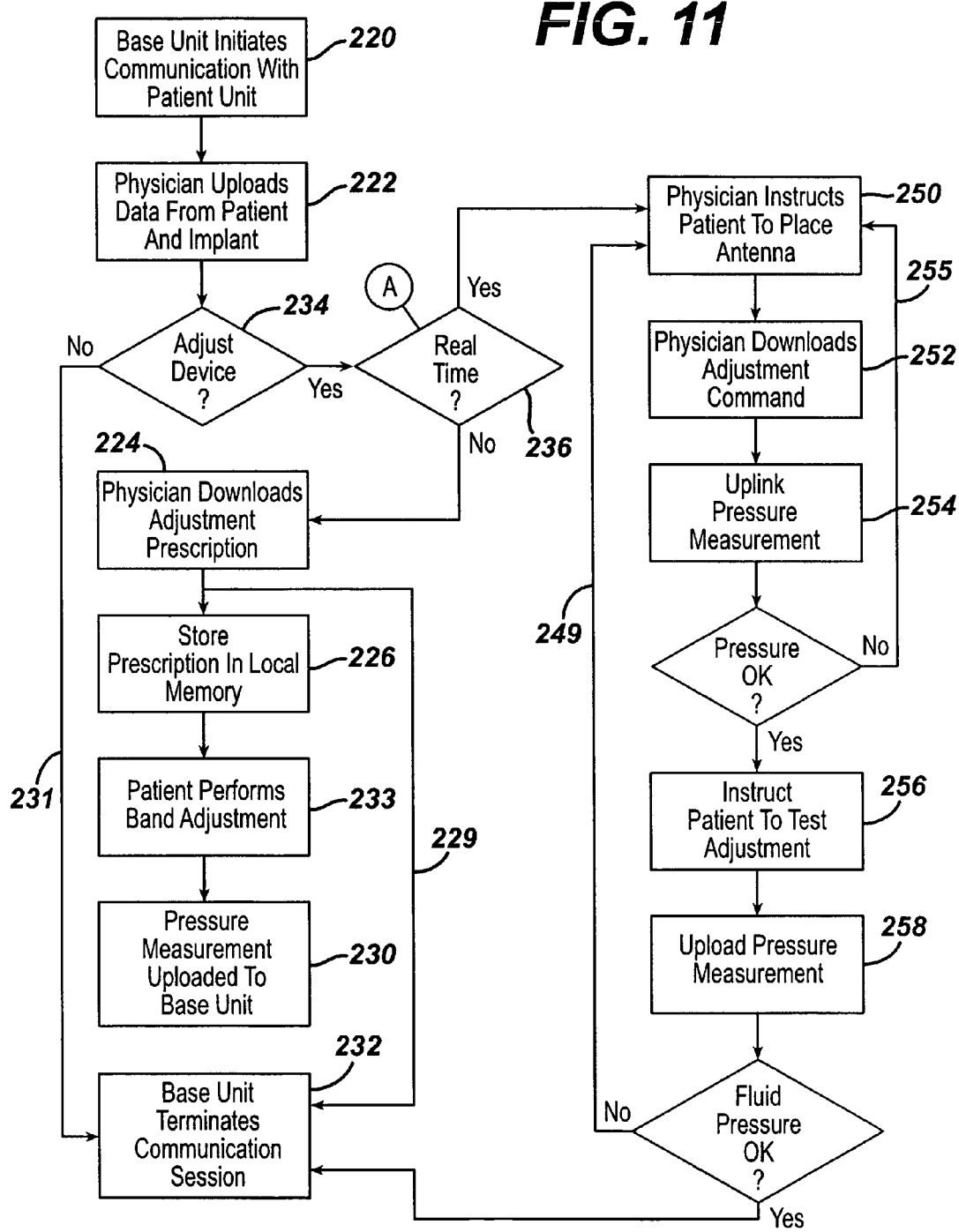
FIG. 11 is a flow diagram of an exemplary communication protocol between the local and remote units for a remotely adjustable restriction device.

In a second exemplary interaction, shown in FIG. 11, the physician downloads an adjustment prescription for a remotely adjustable device, such as infuser 115 shown in FIG. 6. The physician initiates this communication session through link 180 as shown at step 220. After initiating communications, the physician uploads previously stored data, such as fluid pressure histories, from memory 138 of local unit 60. The physician evaluates the data and determines whether an adjustment is indicated. If the physician chooses an off-line adjustment, an adjustment command is downloaded to local unit 60 and stored in memory 138, as indicated in step 224. With the prescription stored in memory 138, the patient, at his convenience, places antenna 54 over the implant area and initiates the adjustment through local unit 60, as indicated in step 233. Local unit 60 then transmits power and command signals to the implanted microcontroller 106 to execute the adjustment. After the adjustment, the patient establishes a communication link with remote monitoring unit 170 and uploads a series of pressure measurements from the implant to the remote unit. These pressure measurements may be stored in memory 174 of remote unit 170 until accessed by the physician.

In an alternative scenario, the patient may perform a real-time adjustment during a virtual treatment session with the physician. In this situation, the physician establishes communication with the patient through link 180. Once connected through link 180, the physician instructs the patient to place antenna 54 over the implant area, as shown at step 250. After antenna 54 is in position, the physician downloads an adjustment command to infuser 115 through link 180, as shown at step 252. During and/or after the adjustment is executed in infuser 115, a series of pressure measurements are uplinked from infuser 115 to the physician through link 180, as shown at step 254. The physician performs an immediate review of the fluid pressure changes resulting from the adjustment. If the resulting fluid pressure levels are too high or too low, the physician may immediately readjust the restriction band, as indicated by line 255. The physician may also instruct the patient to perform a particular action to test the adjustment, such as drinking or eating, as shown at step 256. As the patient performs the test, the physician may upload pressure measurements from the pressure sensor, as shown at step 258, to evaluate the peristaltic pressure against the band as the patient attempts to pass food or liquid through the stoma. If the pressure measurements are too high, indicating a possible obstruction, the physician may immediately transmit additional command signals to readjust the band and relieve the obstruction, as indicated by line 259. After the physician is satisfied with the results of the adjustment, the communication session is terminated at step 232. In the present invention, local unit 60 is at all times a slave to remote unit 170 so that only a physician can prescribe adjustments, and the patient is prevented from independently executing adjustments through local unit 60.

Figure 12:
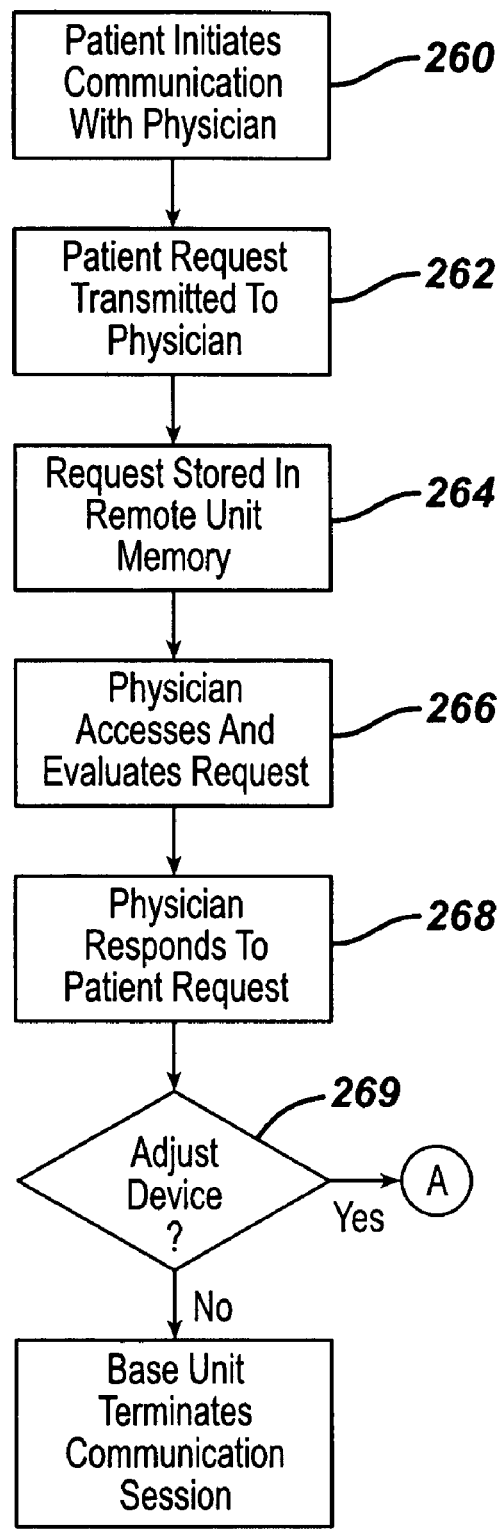
FIG. 12 is a flow diagram of an exemplary communication protocol in which communication is initiated by the patient.

In a third exemplary communication session, shown in FIG. 12, a patient may initiate an interaction with remote unit 170 by entering a request through user interface 140, as shown at step 260. This request may be in the form of an e-mail or other electronic message. At step 262, the patient's request is transmitted through communication link 180 to remote unit 170. At remote unit 170, the patient's request is stored in memory 174 until retrieved at the physician's convenience (step 264). After the physician has reviewed the patient's request (step 266), instructions may be entered through user interface 176 and downloaded to local unit 60. The physician may communicate with the patient regarding treatment or the decision to execute or deny a particular adjustment request, as shown at step 268. If the physician determines at step 269 that an adjustment is required, the physician may initiate a communication session similar to those shown in the flow diagrams of FIGS. 10 and 11. If an adjustment is not indicated, the base unit terminates the session following the responsive communication of step 268.

In addition to the above scenarios, a physician may access local unit 60 at any time to check on patient compliance with previous adjustment instructions, or to remind the patient to perform an adjustment. In these interactions, the physician may contact local unit 60 to request a data upload from memory 138, or transmit a reminder to be stored in memory 138 and displayed the next time the patient turns on local unit 60. Additionally, local unit 60 can include an alarm feature to remind the patient to perform regularly scheduled adjustments, such as diurnal relaxations.

Figure 13:
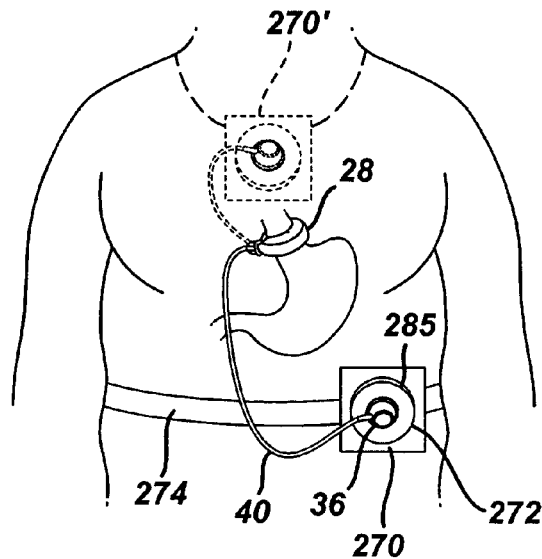
FIG. 13 is a simplified schematic diagram of a data logger for recording pressure measurements from the implanted restriction device.

As mentioned above, communication system 20 can be used to uplink a fluid pressure history to remote unit 170 to allow the physician to evaluate the performance of device 22 over a designated time period. FIG. 13 illustrates a data logger 270 that may be used in conjunction with communication system 22 of the present invention to record fluid pressure measurements over a period of time. In this example, data logger 270 is external to the patient, and is positioned over the region under which injection port 36 is implanted within the patient. In another embodiment, data logger 270 is also implanted within the patient. As shown in FIG. 13, data logger 270 comprises TET and telemetry coils 285, 272 which may be worn by the patient so as to lie adjacent to implanted portion 24. TET coil 285 provides power to the implant, while telemetry coil 272 interrogates the implant and receives data signals, including fluid pressure measurements, through secondary telemetry coil 114. In another embodiment, TET coil 285 and telemetry coil 272 are consolidated into a single coil, and alternate between TET and telemetry functions at any suitable rate for any suitable durations.

The fluid pressure within the restriction band 28 is repeatedly sensed and transmitted to data logger 270 at an update rate sufficient to measure peristaltic pulses against the band. Typically, this update rate is in the range of 10-20 pressure measurements per second. As shown in FIG. 13, data logger 270 may be worn on a belt 274 about the patient's waist to position coils 272 adjacent injection port 36 when the port is implanted in the patient's abdominal area. Alternatively, data logger 270 can be worn about the patient's neck, as shown by device 270', when injection port 36 is implanted on the patient's sternum. Data logger 270 is worn during waking periods to record fluid pressure variations during the patient's meals and daily routines. At the end of the day, or another set time period, data logger 270 may be removed and the recorded fluid pressure data downloaded to memory 138 of local unit 60. The fluid pressure history may be uploaded from memory 138 to remote unit 170 during a subsequent communication session. Alternatively, fluid pressure data may be directly uploaded from data logger 270 to remote unit 170 using communication link 180.

Figure 14:
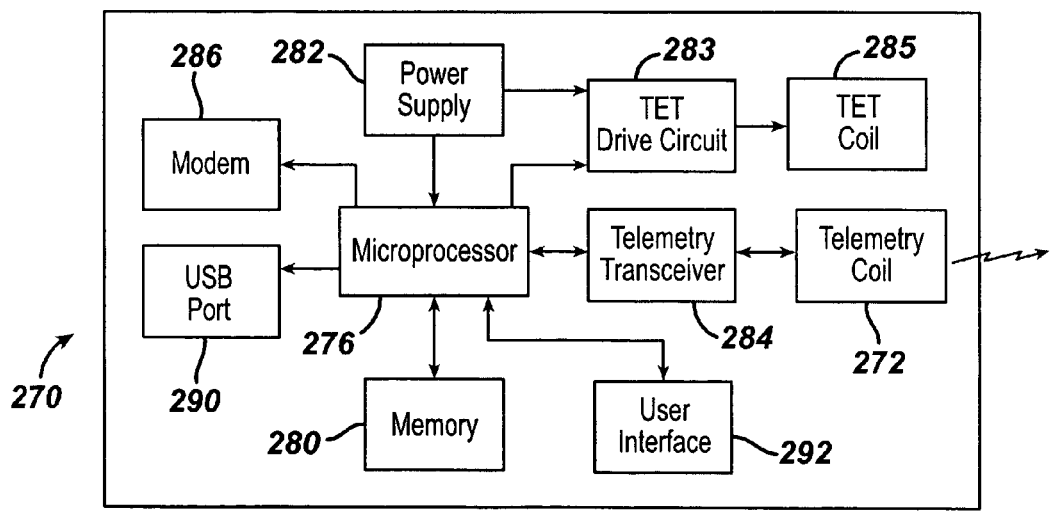
FIG. 14 is a block diagram illustrating the major components of the data logger shown in FIG. 13.

FIG. 14 shows data logger 270 in greater detail. As shown in FIG. 14, data logger 270 includes a microprocessor 276 for controlling telemetry communications with implanted device 24. Microprocessor 276 is connected to a memory 280 for, among other functions, storing pressure measurements from device 24. In the present example, memory 280 comprises 40 Mb of SRAM and is configured to store 100 hours of time stamped pressure data. Of course, any other type of memory 280 may be used, and memory 280 may store any amount of and any other type of data. By way of example only, any other type of volatile memory or any type of non-volatile memory may be used, including but not limited to flash memory, hard drive memory, etc. While data logger 270 of the present example is operational, fluid pressure is read and stored in memory 280 at a designated data rate controlled by microprocessor 276. Microprocessor 276 is energized by a power supply 282. In one embodiment, power supply 282 comprises a rechargeable cell (not shown), such as a rechargeable battery. In one version of this embodiment, the rechargeable cell is removable and may be recharged using a recharging unit and replaced with another rechargeable cell while the spent cell is recharging. In another version of this embodiment, the rechargeable cell is recharged by plugging a recharging adapter into a data logger 270 and a wall unit. In yet another version of this embodiment, the rechargeable cell is recharged wirelessly by a wireless recharging unit. In another embodiment, power supply 282 comprises an ultra capacitor, which may also be recharged. Of course, any other type of power supply 282 may be used.

To record fluid pressure, microprocessor 276 initially transmits a power signal to implanted portion 24 via TET drive circuit 283 and TET coil 285. After the power signal, microprocessor 276 transmits an interrogation signal to implanted portion 24 via telemetry transceiver 284 and telemetry coil 272. The interrogation signal is intercepted by telemetry coil 114 and transmitted to microcontroller 106. Microcontroller 106 sends a responsive, temperature-adjusted pressure reading from sensor 84 via transceiver 158 and secondary telemetry coil 114. The pressure reading is received through coil 272 and directed by transceiver 284 to microprocessor 276. Microprocessor 276 subsequently stores the pressure measurement and initiates the next interrogation request.

When the patient is finished measuring and recording fluid pressure, logger 270 is removed and the recorded pressure data downloaded to local unit 60, or directly to remote unit 170. As shown in FIGS. 9 and 14, data logger 270 may comprise a modem 286 for transmitting the sensed fluid pressure directly to remote unit 170 using a telephone line 288. The patient may connect logger modem 286 to a telephone line, dial the physician's modem, and select a "send" button on user interface 292. Once connected, microprocessor 276 transmits the stored pressure history through the phone line to microprocessor 172 in remote unit 170. Alternatively, data logger 270 may include a USB port 290 for connecting the logger to local unit 60. Logger USB port 290 may be connected to a USB port 198 on local unit 60 (shown in FIG. 8), and the "send" switch activated to download pressure data to memory 138 in the local unit. After the pressure data is downloaded, logger 270 may be turned off through user interface 292, or reset and placed back on the patient's body for continued pressure measurement.

Figure 15:
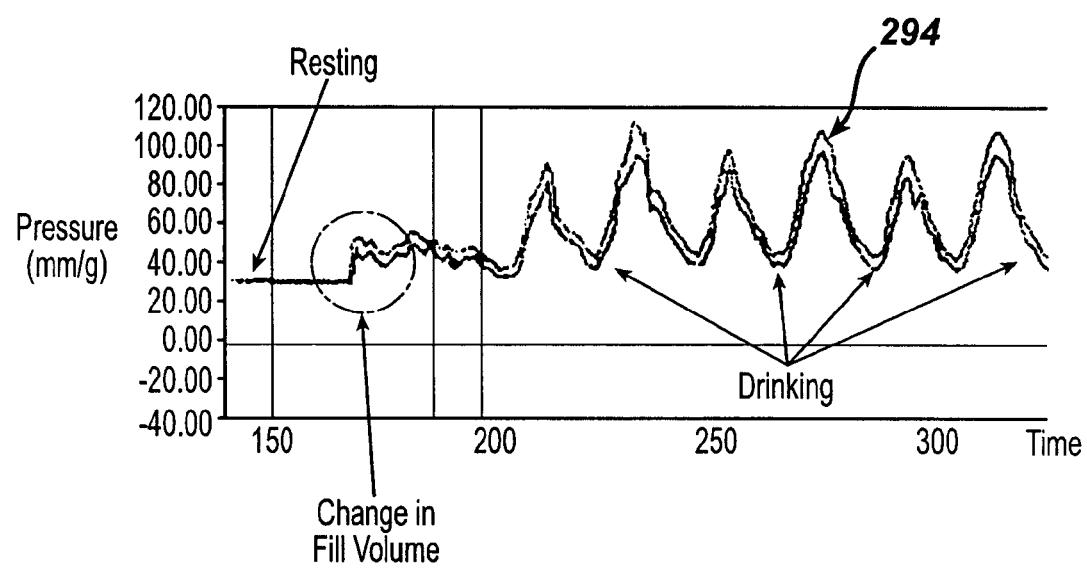
FIG. 15 is a graphical representation of a fluid pressure measurement from the sensor shown in FIG. 4, as communicated through the system of the present invention.

FIG. 15 is a graphical representation of an exemplary pressure signal 294 as measured by sensor 84 during repeated interrogation by local unit 60 or data logger 270 over a sampling time period. Pressure signal 294 may be displayed using graphical user interface 140 of local unit 60 or graphical user interface 176 of remote unit 170. In the example shown in FIG. 15, the fluid pressure in band 28 is initially measured while the patient is stable, resulting in a steady pressure reading as shown. Next, an adjustment is applied to band 28 to decrease the stoma size. During the band adjustment, pressure sensor 84 continues to measure the fluid pressure and transmit the pressure readings through the patient's skin to local unit 60. As seen in the graph of FIG. 15, fluid pressure rises following the band adjustment.

In the example shown, the patient is asked to drink a liquid after the adjustment to check the accuracy of the adjustment. As the patient drinks, pressure sensor 84 continues to measure the pressure spikes due to the peristaltic pressure of swallowing the liquid. The physician may evaluate these pressure spikes from a remote location in order to evaluate and direct the patient's treatment. If the graph indicates pressure spikes exceeding desired levels, the physician may immediately take corrective action through communication system 20, and view the results of the corrective action, until the desired results are achieved. Accordingly, through communication system 20 a physician can perform an adjustment and visually see the results of the adjustment, even when located at a considerable distance from the patient.

In addition to adjustments, communication system 20 can be used to track the performance of an intake restriction device over a period of time. In particular, a sampling of pressure measurements from data logger 270 may be uploaded to the physician's office for evaluation. The physician may visually check a graph of the pressure readings to evaluate the performance of the restriction device. It will be appreciated that long term pressure data may be helpful in seeing when the patient eats or drinks during the day and how much. Such data may thus be useful in compliance management.

Pressure measurement logs can also be regularly transmitted to remote monitoring unit 170 to provide a physician with a diagnostic tool to ensure that a food intake restriction device is operating effectively. For instance, pressure data may be helpful in seeing how much band 28 pressure or tightness varies, and if band 28 tends to obstruct at times. If any abnormalities appear, the physician may use communication system 20 to contact the patient and request additional physiological data, prescribe an adjustment, or, where components permit, administer an adjustment. In particular, communication system 20 may be utilized to detect a no pressure condition within band 28, indicating a fluid leakage. Alternatively, system 20 may be used to detect excessive pressure spikes within band 28 or pressure being stuck at a fixed level, which may indicate a kink in catheter 40 or a blockage within the stoma.

Local unit 60, another type of docking station 360, remote unit 170, or some other device may further comprise a logic that is configured to process pressure data and actively provide an alert to a physician, the patient, or someone else when a dramatic change in pressure is detected or under other predefined conditions. Such an alert may comprise any of the following: an e-mail, a phone call, an audible signal, or any other type of alert. The conditions for and/or type of an alert may also vary relative to the recipient of the alert. For instance, with respect to alerts for physicians, such alerts may be limited to those provided upon an indication that some component of implanted portion 24 has structurally failed (e.g., a kink in catheter 40, a burst band 28, etc.). With respect to alerts for patients, such alerts may be limited to those provided upon an indication that the patient is eating too much, eating to quickly, or if the bite sizes are too big. A variety of other conditions under which alerts may be directed to a physician or patient will be apparent to those of ordinary skill in the art. In addition, it will be appreciated that physicians and patients may receive alerts under similar conditions, or that either party may simply not receive alerts at all.

To the extent that local unit 60 has a graphical user interface permitting the patient to see pressure data, local unit 60 may be used by the patient to evaluate pressure readings at home and notify their physician when the band 28 pressure drops below a specified baseline, indicating the need for an adjustment of the device. Communication system 20 thus has benefits as a diagnostic and monitoring tool during patient treatment with a bariatric device. The convenience of evaluating an intake restriction device 22 through communication system 20 facilitates more frequent monitoring and, components permitting, adjustments of the device.

Figure 16:
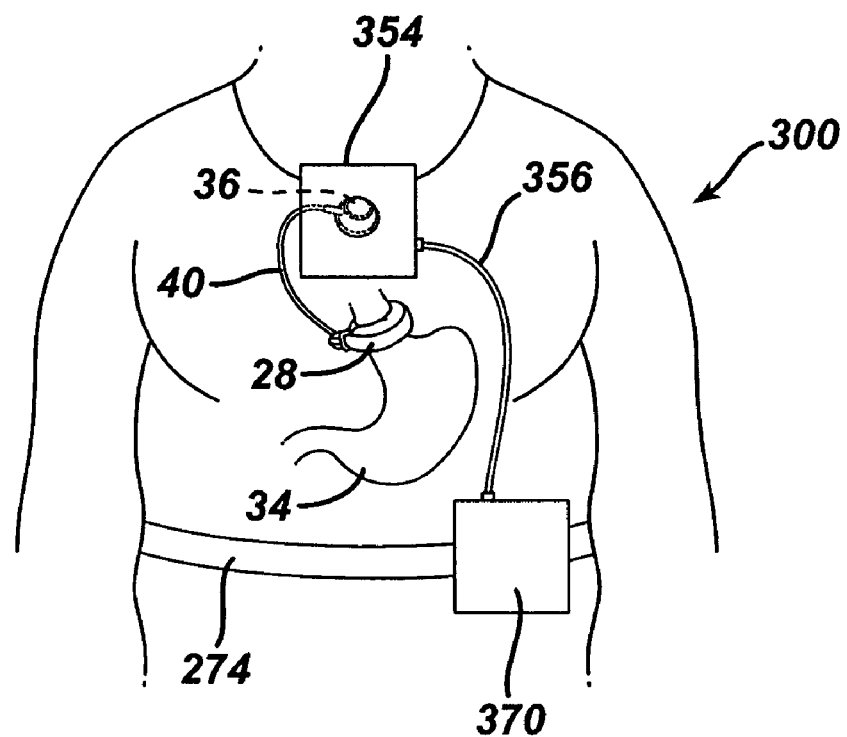
FIG. 16 is a simplified schematic diagram of a data logging system for recording pressure measurements from the food intake restriction device shown in FIG. 1.

An alternate embodiment of a data logging system 300 is shown in FIG. 16. In this example, data logging system 300 comprises a coil head 354 and a data logger 370. Coil head 354 and data logger 370 are in communication via a cable 356. Cable 356 is detachable from coil head 354 and data logger 370. Of course, it will be appreciated that cable 356 is merely exemplary, and that any suitable alternative may be used, including but not limited to a wireless transmitter/receiver system. In the present example, coil head 354 is worn around the neck of the patient, and is positioned generally over injection port 36. Data logger 370 is worn on a belt 274 about the patient's waist. Of course, these respective locations are merely exemplary, and it will be appreciated that coil head 354 and data logger 370 may be positioned elsewhere. By way of example only, where injection port 36 is implanted in the patient's abdomen, coil head 354 may be worn on a belt 274. It will also be appreciated that coil head 354 and data logger 370 are represented as simple blocks in FIG. 16 for illustrative purposes only, and that either of coil head 354 or data logger 370 may be provided in a variety of shapes, sizes, and configurations.

Figure 17:
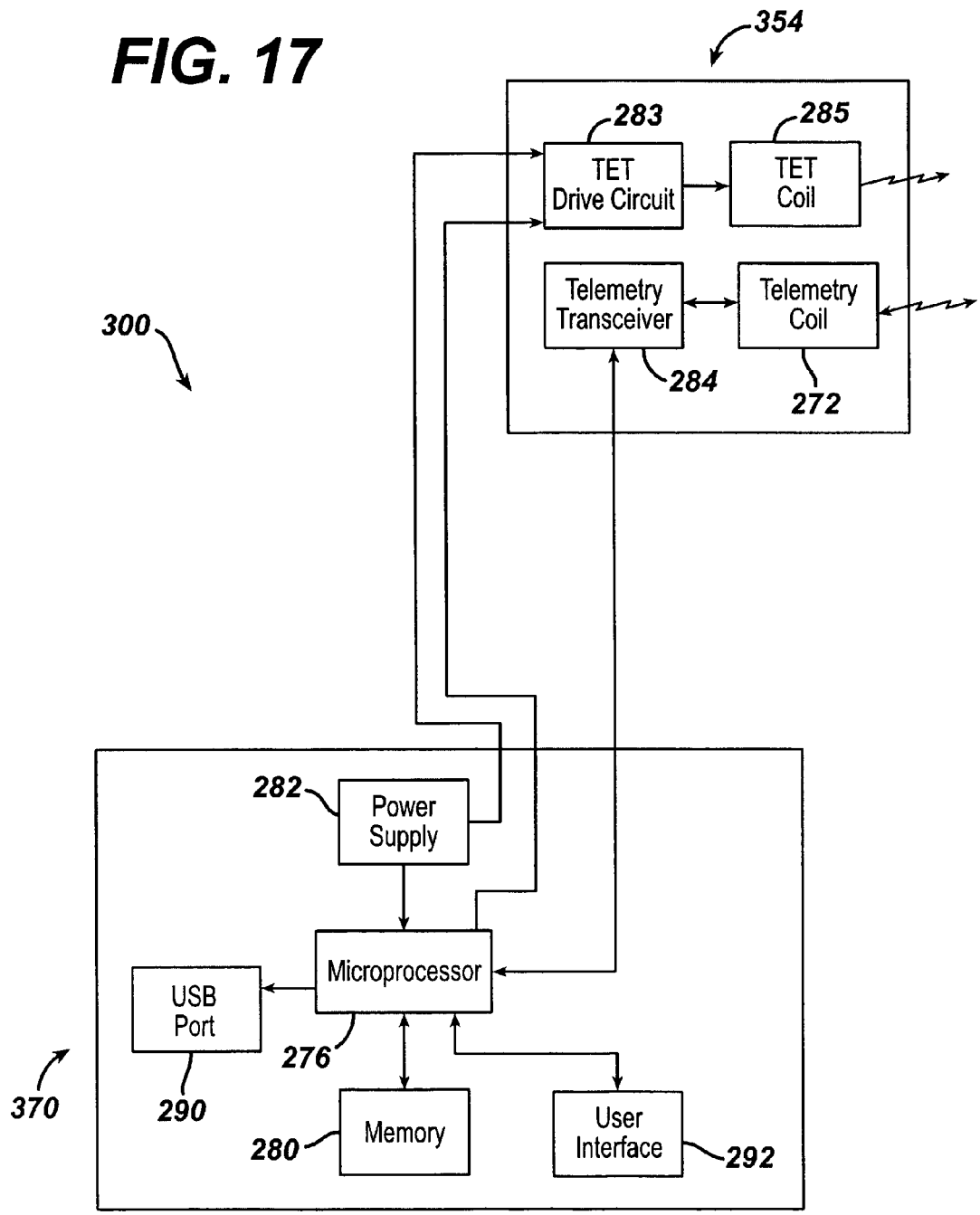
FIG. 17 is a block diagram illustrating several components of the data logging system shown in FIG. 16.

Exemplary components of data logging system 300 are shown in FIG. 17. As shown, data logger 370 comprises a microprocessor 276, a memory 280, a power supply 282, a USB port 290, and a user interface 292. Coil head 354 comprises a TET drive circuit 283, a telemetry transceiver 284, a TET coil 285, and a telemetry coil 272. TET drive circuit 283 is configured to receive power from power supply 282 via cable 356. TET drive circuit is further configured to receive signals from microprocessor 276 via cable 356. Telemetry transceiver 284 is configured to receive signals from microprocessor 276, and transmit signals to microprocessor 276, via cable 356. In another embodiment, telemetry transceiver 284 is configured to only transmit signals to microprocessor 276. It will be appreciated that many of the components depicted in FIG. 17 are similar to those depicted in FIG. 14 and described in the accompanying text. Accordingly, the above discussion of such components with reference to FIG. 14 may also be applied to the components shown in FIG. 17. In the present example, coil head 354 and data logger 370 may be viewed as a separation of components comprising data logger 270 (described above) into two physically separate units. It will further be appreciated that any of the components shown in FIG. 17, as well as their relationships, functions, etc., may be varied in any suitable way.

In the present example, coil head 354 is configured similar to and functions in a manner similar to antenna 54 described above. TET coil 285 of coil head 354 is configured to provide power to injection port 36. Of course, to the extent that any other devices (e.g., a pump, etc.) are implanted in the patient that are configured to receive power from a TET coil 285, TET coil 285 may also provide power to such devices. Power provided by TET coil 285 may be provided to TET coil 285 by and regulated by TET drive circuit 285, which may itself receive power from power supply 282 via cable 356. Such power provided to TET drive circuit 283 may be regulated by microprocessor 276 via cable 356. In addition, or in the alternative, microprocessor 276 may regulate the manner in which TET drive circuit 285 provides power to TET coil 285. Other suitable configurations and relationships between these components, as well as alternative ways in which they may operate, will be apparent to those of ordinary skill in the art. It will also be appreciated that, while the present example contemplates the use of RF signaling through TET coil 285, any other type of powering technique, as well as alternative power communicators, may be used.

Telemetry coil 272 of coil head 354 is configured to receive signals from coil 114 of injection port 36, including signals indicative of the pressure of fluid within the implanted device (e.g., pressure of fluid within the injection port 36, within catheter 40, and/or within adjustable band 28, pressure obtained using pressure sensor 84, etc.) and signals indicative of temperature. It will be appreciated that telemetry coil 272 may also receive any other type of signal representing any other type of information from any other source. Signals received by telemetry coil 272 are communicated to telemetry transceiver 284, which is configured to communicate such signals to microprocessor 276 via cable 356. Telemetry transceiver 284 may perform any appropriate translation or processing of signals received from telemetry coil 272 before communicating signals to microprocessor 276. Other suitable configurations and relationships between these components, as well as alternative ways in which they may operate, will be apparent to those of ordinary skill in the art. It will also be appreciated that components may be combined. By way of example only, TET coil 285 and telemetry coil 272 may be consolidated into a single coil, and alternate between TET and telemetry functions at any suitable rate for any suitable durations. In addition, while the present example contemplates the use of RF signaling through telemetry coil 272, it will be appreciated that any other type of communication technique (e.g., ultrasonic, magnetic, etc.), as well as alternative communicators other than a coil, may be used.

Data logger 370 may receive pressure measurements throughout a given day, and store the same in memory 280, thereby recording fluid pressure variations during the patient's meals and daily routines. In the present example, memory 280 comprises 40 Mb of SRAM and is configured to store 100 hours of time stamped pressure data. Of course, any other type of memory 280 may be used, and memory 280 may store any amount of and any other type of data. By way of example only, any other type of volatile memory or any type of non-volatile memory may be used, including but not limited to flash memory, hard drive memory, etc. While data logger 370 of the present example is operational, fluid pressure is read and stored in memory 280 at a designated data rate controlled by microprocessor 276. In one embodiment, fluid pressure is repeatedly sensed and transmitted to data logger 370, then stored in memory 280, at an update rate sufficient to measure peristaltic pulses against adjustable band 28. By way of example only, the update rate may range between approximately 10-20 pressure measurements per second. Other suitable update rates may be used.

In another embodiment, implanted portion 24 comprises a memory (not shown). By way of example only, such implanted memory may be located in injection port 36 or elsewhere. Such implanted memory may be used for a variety of purposes, to the extent that such memory is included. For instance, such implanted memory may store the same data as memory 280 of data logger 370, such that implanted memory provides a backup for memory 280 of data logger 370. In this version, such data may be further retained in implanted memory for archival purposes, may be replaced on a daily basis, may be replaced or updated after data logger 370 transmits the same data to remote unit 170, or may otherwise be used. It will also be appreciated that an implanted memory may be used to store pre-selected information or pre-selected types of information. For instance, an implanted memory may store maximum and minimum pressure measurements, fluoroscopic images or video of a patient swallowing, and/or any other information. Other information suitable for storing in an implanted memory will be apparent to those of ordinary skill in the art. It will also be appreciated that any type of memory may be implanted, including but not limited to volatile (e.g., SRAM, etc.), non-volatile (e.g., flash, hard drive, etc.), or other memory.

In the present example, microprocessor 276 is energized by a power supply 282. In one embodiment, power supply 282 comprises a rechargeable cell (not shown), such as a rechargeable battery. In one version of this embodiment, the rechargeable cell is removable and may be recharged using a recharging unit and replaced with another rechargeable cell while the spent cell is recharging. In another version of this embodiment, the rechargeable cell is recharged by plugging a recharging adapter into a data logger 370 and a wall unit. In yet another version of this embodiment, the rechargeable cell is recharged wirelessly by a wireless recharging unit. In another embodiment, power supply 282 comprises an ultra capacitor, which may also be recharged. Of course, any other type of power supply 282 may be used.

Data logger 370 of the present example may be configured to provide an alert to the patient under a variety of circumstances in a variety of ways. For instance, data logger 370 may provide an audible and/or visual alert when there is a drastic change in fluid pressure. Alternatively, data logger 370 may provide an audible and/or visual alert upon a determination, based at least in part on pressure data, that the patient is eating too much, too quickly, etc. Data logger 370 may also alert the patient upon a determination that coil head 354 is not communicating with injection port 36 properly. Still other conditions under which a patient may be alerted by data logger 370 will be apparent to those of ordinary skill in the art. It will also be appreciated that user interface 292 may comprise any number or types of features, including but not limited to a speaker, an LED, and LCD display, an on/off switch, etc. In the present example, user interface 292 is configured to provide only output to the patient, and does not permit the patient to provide input to data logger 370. User interface 292 of the present example thus consists of a green LED to show that the power supply 282 is sufficiently charged and a red LED to show that the power supply 282 needs to be recharged. Of course, user interface 292 may alternatively permit the patient to provide input to data logger 370, and may comprise any suitable components and features.

Figure 18:
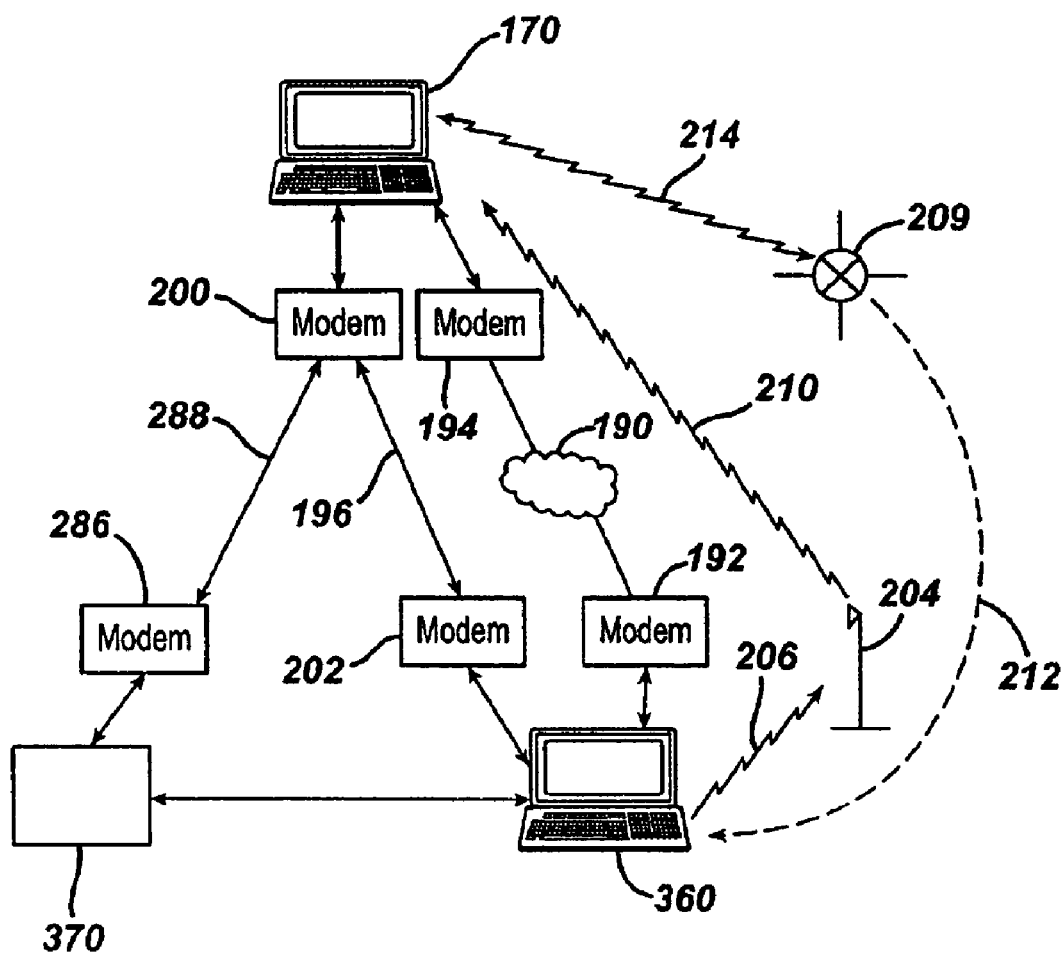
FIG. 18 is a simplified schematic diagram showing the data logging system shown in FIG. 16 in a docking state with a number of different communication links.

As shown in FIG. 18, data logging system 300 further comprises a docking station 360. Docking station 360 is configured to receive data communications from data logger 370, and is further configured to transmit data communications to remote unit 170. In the present example, data logger 370 comprises a USB port 290, such that docking station 360 may receive communications from data logger 370 via a USB cable (not shown) coupled with USB port 290. In one embodiment, docking station 360 comprises the patient's personal computer. Of course, docking station 360 may receive communications from data logger 370 in any other suitable way. For instance, such communications may be transmitted wirelessly (e.g., via RF signals, Bluetooth, ultrawideband, etc.).

In another embodiment, docking station 360 is dedicated to coupling with data logger 370, and comprises a cradle-like feature (not shown) configured to receive data logger 370. In this example, the cradle-like feature includes contacts configured to electrically engage corresponding contacts on data logger 370 to provide communication between docking station 360 and data logger 370. Docking station 360 may thus relate to data logger 370 in a manner similar to docking systems for personal digital assistants (PDAs), BLACKBERRY® devices, cordless telephones, etc. Other suitable ways in which data logger 370 and docking station 360 may communicate or otherwise engage will be apparent to those of ordinary skill in the art. It will also be appreciated that docking station 360 is depicted in FIG. 18 as a desktop computer for illustrative purposes only, and that docking station 360 may be provided in a variety of alternative shapes, sizes, and configurations.

In one embodiment, docking station 360 comprises local unit 60 described above. Accordingly, it will be appreciated that the above discussion referring to components depicted in FIG. 9 may also be applied to components depicted in FIG. 18. Similarly, methods such as those shown in FIGS. 10-12 and described in accompanying text may also be implemented with docking station 360. In another embodiment, data logger 370 comprises local unit 60. In yet another embodiment, data logger 370 is provided with an AC adapter or similar device operable to recharge power supply 282, and data logger 370 further comprises an Ethernet port (not shown) enabling data logger 370 to be connected directly to a network such as the Internet for transmitting information to remote unit 170. It will therefore be appreciated that any of the features and functions described herein with respect to local unit 60 and/or docking station 360 may alternatively be incorporated into data logger 370 or may be otherwise allocated.

In one exemplary use, the patient wears coil head 354 and data logger 370 throughout the day to record pressure measurements in memory 280. At night, the patient decouples data logger 370 from coil head 354 and couples data logger 370 with docking station 360. While data logger 370 and docking station 360 are coupled, docking station 360 transmits data received from data logger 370 to remote unit 170. To the extent that power supply 282 comprises a rechargeable cell, docking station 360 may be further configured to recharge the cell while data logger 370 is coupled with docking station 360. Of course, it will be immediately apparent to those of ordinary skill in the art that a patient need not necessarily decouple data logger 370 from coil head 354 in order to couple data logger 370 with docking station 360. It will also be appreciated that pressure measurements may be recorded in memory 280 during the night in addition to or as an alternative to recording such measurements during the day, and that pressure measurements may even be recorded twenty four hours a day. It is thus contemplated that the timing of pressure measurement taking and recordation need not be limited to the daytime only. It is also contemplated that every pressure measurement that is taken need not necessarily be recorded.

As described above, data logger 370 is configured to receive, store, and communicate data relating to the pressure of fluid. However, data logger 370 may receive, store, and/or communicate a variety of other types of data. By way of example only, data logger 370 may also receive, process, store, and/or communicate data relating to temperature, EKG measurements, eating frequency of the patient, the size of meals eaten by the patient, the amount of walking done by the patient, etc. It will therefore be appreciated that data logger 370 may be configured to process received data to create additional data for communicating to docking station 360. For instance, data logger 370 may process pressure data obtained via coil head 354 to create data indicative of the eating frequency of the patient. It will also be appreciated that data logger 370 may comprise additional components to obtain non-pressure data. For instance, data logger 370 may comprise a pedometer or accelerometer (not shown) to obtain data relating to the amount of walking done by the patient. Data obtained by such additional components may be stored in memory 280 and communicated to docking station 360 in a manner similar to pressure data. Data logger 370 may also comprise components for obtaining data to be factored in with internal fluid pressure measurements to account for effects of various conditions on the fluid pressure. For instance, data logger 370 may comprise a barometer for measuring atmospheric pressure. In another embodiment, data logger 370 comprises an inclinometer or similar device to determine the angle at which the patient is oriented (e.g., standing, lying down, etc.), which may be factored into pressure data to account for hydrostatic pressure effects caused by a patient's orientation. Alternatively, an inclinometer or other device for obtaining non-pressure data may be physically separate from data logger 370 (e.g., implanted). Still other types of data, ways in which such data may be obtained, and ways in which such data may be used will be apparent to those of ordinary skill in the art.

It will be appreciated that several embodiments described herein may enable health care providers or others to use pressure data as a feedback mechanism to identify, train, and/or prescribe dietary advice to a patient. Such a feedback mechanism may provide data or otherwise be used in multiple ways. For instance, pressure feedback may be obtained when a patient swallows a particular food portion, and based on such pressure feedback, the patient may be taught to eat smaller portions, larger portions, or portions equal to the portion tested. Of course, a food portion so prescribed may be tested by evaluating pressure feedback obtained when the patient swallows the prescribed food portion, such that a food portion prescription may be refined through reiteration. As another example, a patient may test desired foods for appropriateness based on pressure feedback together with portion size and/or based on any other parameters. It will also be appreciated that continuous pressure data monitoring may be used to enable portion size monitoring, food consistency monitoring (e.g., liquids vs. solids) and/or eating frequency. Still other ways in which pressure data may be used to provide dietary advice will be apparent to those of ordinary skill in the art. It will also be appreciated that such uses may be practiced locally, remotely (e.g., via remote unit 170), or combinations thereof.

While data logging system 300 is described herein as being implemented with injection port 36, it will be appreciated that data logging system 300 may alternatively be implemented with any other type of pressure sensing system or other implanted systems. By way of example only, data logging system 300 may be combined with any of the pressure sensing devices disclosed in U.S. Non-Provisional patent application Ser. No. 11/369,682, filed Mar. 7, 2006, and entitled "System and Method for Determining Implanted Device Positioning and Obtaining Pressure Data," the disclosure of which is incorporated by reference herein for illustrative purposes. For instance, data logging system 300 may receive pressure measurements obtained by any of the pressure sensors described in that patent application. In addition, the needle guidance sense head described in that patent application may be used with at least a portion of data logging system 300 to provide needle guidance for a local clinician to adjust fluid pressure in accordance with a remote physician's instructions that are based on pressure measurements obtained by the needle guidance sense head and communicated to the remote physician in substantially real-time. For instance, the needle guidance sense head may be coupled with data logger 370, which may connected directly to the Internet (or via docking station 360) to provide pressure measurements to the remote physician. Still other ways in which devices and components described herein may be combined with components described in U.S. Non-Provisional patent application Ser. No. 11/369,682 will be apparent to those of ordinary skill in the art.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated with respect to transmitting pressure data from the implant to the remote monitoring unit. However, other types of data may also be transmitted to enable a physician to monitor a plurality of different aspects of the restrictive opening implant. Additionally, the present invention is described with respect to a food intake restriction device for bariatric treatment. The present invention is not limited to this application, and may also be utilized with other restrictive opening implants or artificial sphincters without departing from the scope of the invention. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. A system for obtaining data from an implanted device, the system comprising:
   (a) an implantable restriction forming device, wherein the implantable restriction forming device is operable to form a restriction in a patient, wherein the implantable restriction forming device comprises an implantable injection port, wherein the implantable injection port defines a fluid reservoir in fluid communication with the implantable restriction forming device, wherein the fluid reservoir of the implantable injection port is configured to receive a fluid, wherein the implantable injection port includes a needle penetrable septum configured to receive a needle for adding fluid to or withdrawing fluid from the fluid reservoir via the needle;
   (b) an implantable pressure sensor positioned within the implantable injection port of the implantable restriction forming device, wherein the implantable pressure sensor comprises a diaphragm in fluid communication with the fluid reservoir of the implantable injection port and one or more strain gauges connected with the diaphragm, wherein the one or more strain gauges are configured to sense strain in the diaphragm as a function of the pressure of the fluid such that the implantable pressure sensor is operable to sense the pressure of fluid in the fluid reservoir;
   (c) one or more implantable communicators in communication with the implantable pressure sensor, wherein the one or more implantable communicators are operable to communicate data from within a patient;
   (d) one or more external communicators in communication with the one or more implantable communicators, wherein the one or more external communicators are operable to externally receive data communicated from within a patient by the one or more implantable communicators; and
   (e) a storage device in communication with the one or more external communicators, wherein the storage device is operable to store at least a portion of data received by the one or more external communicators.

2. The system of claim 1, wherein the implantable restriction forming device further comprises an adjustable gastric band in fluid communication with the implantable injection port.

3. The system of claim 1, wherein one or both of the one or more implantable communicators or the one or more external communicators comprise at least one coil.

4. The system of claim 1, further comprising a data logger in communication with the one or more external communicators, wherein the storage device is located within the data logger, wherein the data logger is operable to provide a source of energy to the one or more external communicators.

5. The system of claim 4, further comprising a sense head, wherein the one or more external communicators are located within the sense head.

6. The system of claim 5, wherein the data logger and the sense head are located in separate housings connected via a cable.

7. The system of claim 4, wherein the data logger comprises a rechargeable cell, wherein the rechargeable cell is configured to provide power to the one or more external communicators.

8. The system of claim 7, further comprising a docking station, wherein the data logger is configured to selectively couple with the docking station, wherein the docking station is configured to recharge the rechargeable cell.

9. The system of claim 8, wherein the docking station further comprises a communication port in communication with the storage device, wherein the communication port is configured to communicate with a remote monitoring unit via the network.

10. The system of claim 1, further comprising a communication port in communication with the storage device, wherein the communication port is configured to communicate with a remote monitoring unit via the network.

11. A system for obtaining data from an implantable restriction forming device, the system comprising:
   (a) a gastric band having an inflatable member, the inflatable member being configured to receive fluid, the gastric band being configured to form a restriction in a patient based on the pressure of fluid in the inflatable member;
   (b) an implantable injection port in fluid communication with the inflatable member of the gastric band, wherein the implantable injection port includes a needle penetrable septum configured to receive a needle for adjusting an amount of fluid in the inflatable member via the needle;
   (c) a pressure sensor, wherein the pressure sensor is configured to sense the pressure of fluid in the inflatable member;
   (d) a TET communicator, wherein the TET communicator is operable to provide power to a device implanted within a patient;
   (e) a telemetry communicator, wherein the telemetry communicator is operable to transmit data communicated from the one or more implantable pressure sensors located within the implantable restriction forming device;

(f) a storage device in communication with the telemetry communicator, wherein the storage device is operable to store data transmitted from the telemetry communicator;

(g) a microprocessor in communication with the TET communicator, the telemetry coil, and the storage device, wherein the microprocessor is configured to regulate transmission of data from the telemetry communicator to the storage device; and (h) a patient orientation sensor configured to detect orientation data associated with a patient, wherein the patient orientation sensor is in communication with the microprocessor, wherein the microprocessor is configured to account for hydrostatic effects on the fluid pressure caused by patient orientation as detected by the patient orientation sensor.

12. The system of claim 11, wherein the TET communicator and the telemetry communicator are physically separate communicators.

13. The system of claim 11, further comprising a first housing and a second housing, wherein the TET communicator and the telemetry communicator are located in the first housing, wherein the storage device and the microprocessor are located in the second housing.

14. The system of claim 13, further comprising a docking station, wherein the docking station is operable to engage one or more components of the second housing.

15. The system of claim 14, wherein the docking station is further operable to receive data communicated from the storage device.

* * * * *